(12) United States Patent
Fisher et al.

(10) Patent No.: US 6,737,523 B1
(45) Date of Patent: May 18, 2004

(54) NUCLEIC ACIDS COMPRISING REGIONS OF THE RAT PEG-3 PROMOTER THAT DISPLAY ELEVATED EXPRESSION IN HUMAN CANCER CELLS AND USES THEREOF

(75) Inventors: Paul B. Fisher, Scarsdale, NY (US); Zao-Zhong Su, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/621,781

(22) Filed: Jul. 21, 2000

Related U.S. Application Data

(63) Continuation-in-part of application No. 09/052,753, filed on Mar. 31, 1998, now Pat. No. 6,472,320, which is a continuation-in-part of application No. PCT/US98/05793, filed on Mar. 20, 1998.

(51) Int. Cl.$^7$ .......................... C07H 21/04; C12N 15/00
(52) U.S. Cl. ................... 536/24.1; 435/320.1; 435/455; 435/366
(58) Field of Search ...................... 536/24.1; 435/320.1, 435/455, 366

(56) References Cited

FOREIGN PATENT DOCUMENTS

WO      WO 98/42315     * 10/1998

OTHER PUBLICATIONS

Hollander et al (1997) Journal of Biological Chemistry 272:13731–13737.*
Hollander et al. Database GenEMBL. Accession No. U83984, Jul. 7, 1998. Accessed Apr. 6, 2002.*
Fisher et al. Database GENESEQ. Accession No. AAV65766, Feb. 2, 1999. Accessed Apr. 6, 2002.*
Verma et al (1997) Nature 389:239–242.*
Palu et al (1999) J. Biotechnol. 68: 1–13.*
Luo et al (2000) Nature Biotechnology 18:33–37.*
Fox, ASM News, Feb. 2000, 66 (2): 1–3.*
G.J., Young, C.S.H. and Fisher, P.B., PEG–3, *A Nontransforming Cancer Progression Gene, Is A positive Regulator Of Cancer Aggressiveness and Angiogenesis*, (1999), *Proc. Natl. Acad. Sci. USA*, 96(26):15115–20 (Exhibit B).
Gopalkrishnan, R.V., Christiansen, K., Goldstein, N.I., DePinho, R.A. and Fisher, P.B., *Use Of The Human EF–1 Alpha Promoter For Expression Can Significantly Increase Success In Establishing Stable Cell Lines With Consistent Expression: A Study Using The Tetracycline–inducible System In Human Cancer Cells* (1999) *Nucl. Acids Res.*, 27(24):4775–82 (Exhibit C).

Jiang, H. and Fisher, P.B., (1993) *Use Of A Sensitive And Efficient Subtraction Hybridization Protocol For The Identification Of Genes Differentially Regulated During The Induction Of Differentiation In Human Melanoma Cells, Mol. Cell. Different.*, 1(3):285–299 (Exhibit D).
Kang, D.–c., Motwani, M. and Fisher, P.B., *Role Of The Transcriptional Factor AP–1 In Melanoma Differentiation (Review)*, (1998) *Intl. J. Oncology*, 13:1117–1126 (Exhibit E).
Kang, D.–c., LaFrance, R., Su, Z.–z. and Fisher, P.B., *Reciprocal Subtraction Differential RNA Display: An Efficient And Rapid Procedure For Isolating Differentially Expressed Gene Sequences*, (1998) Proc. *Natl. Acad. Sci. USA*, 95(23):13788 (Exhibit F).
Seth. A., Ascione, R., Fisher, R. J., Mavrothalassitis, G.J., Bhat, N.K. and Papas, T.S., *The ets Gene Family* (1992) *Cell Growth & Different.*, 3(5):327–334 (Exhibit G).
Su, Z.–z., Yemul, S., Estabrook, A., Zimmer, S.G., Friedman, R.M. and Fisher, P.B., *Transcriptional Switching Model For The Regulation Of Tumorigenesis And Metastasis by The Has–ras Oncogene: Transcriptional Changes In The Has–ras Tumor Suppressor Gene Lysyl Oxidase*, (1995) *Intl. J. Oncology*, 7:1279 (Exhibit H).
Su. Z.–z., Shen, R., O'Brian, C.A. and Fisher, P.B., *Induction Of Transformation Progression In Type 5 Adenovirus–transformed Rat Embryo Cells By A Cloned Protein Kinase C Beta 1 Gene And Reversal Of Progression By 5–Azacytidine*, (1994) *Oncogene*, 9(4):1123–32 (Exhibit I).
Su, Z.–z., Shi, Y. and Fisher, P.B., *Subtraction Hybridization Identifies a Transformation Progression–Associated Gene PEG–3 With Sequence Homology To a Growth Arrest And DNA Damage–inducible Gene* (1997) *Proc. Natl. Acad. Sci. USA*, 94:(17) 9125–30 (Exhibit J).

* cited by examiner

Primary Examiner—James Ketter
Assistant Examiner—David Lambertson
(74) Attorney, Agent, or Firm—Baker Botts, L.L.P.

(57) ABSTRACT

This invention provides an isolated nucleic acid comprising a PEG-3 promoter comprising the nucleotide sequence of –270 to +194 of FIG. 2. The invention also provides a method for identifying an agent that modulates PEG-3 promoter activity using a cell which comprises a PEG-3 promoter operatively linked to a reporter gene, wherein reduced reporter gene expression in the presence of the agent is indicative of an agent that inhibits PEG-3 promoter activity and wherein increased reporter gene expression in the presence of the agent is indicative of an agent that enhances PEG-3 promoter activity. The invention provides a method for treating cancer in a subject which comprises administering a nucleic acid comprising a PEG-3 promoter operatively linked to a gene-of-interest, wherein the gene-of-interest is selectively expressed in cancerous cells in the subject and such expression results in growth suppression or death of the cancerous cells.

12 Claims, 13 Drawing Sheets

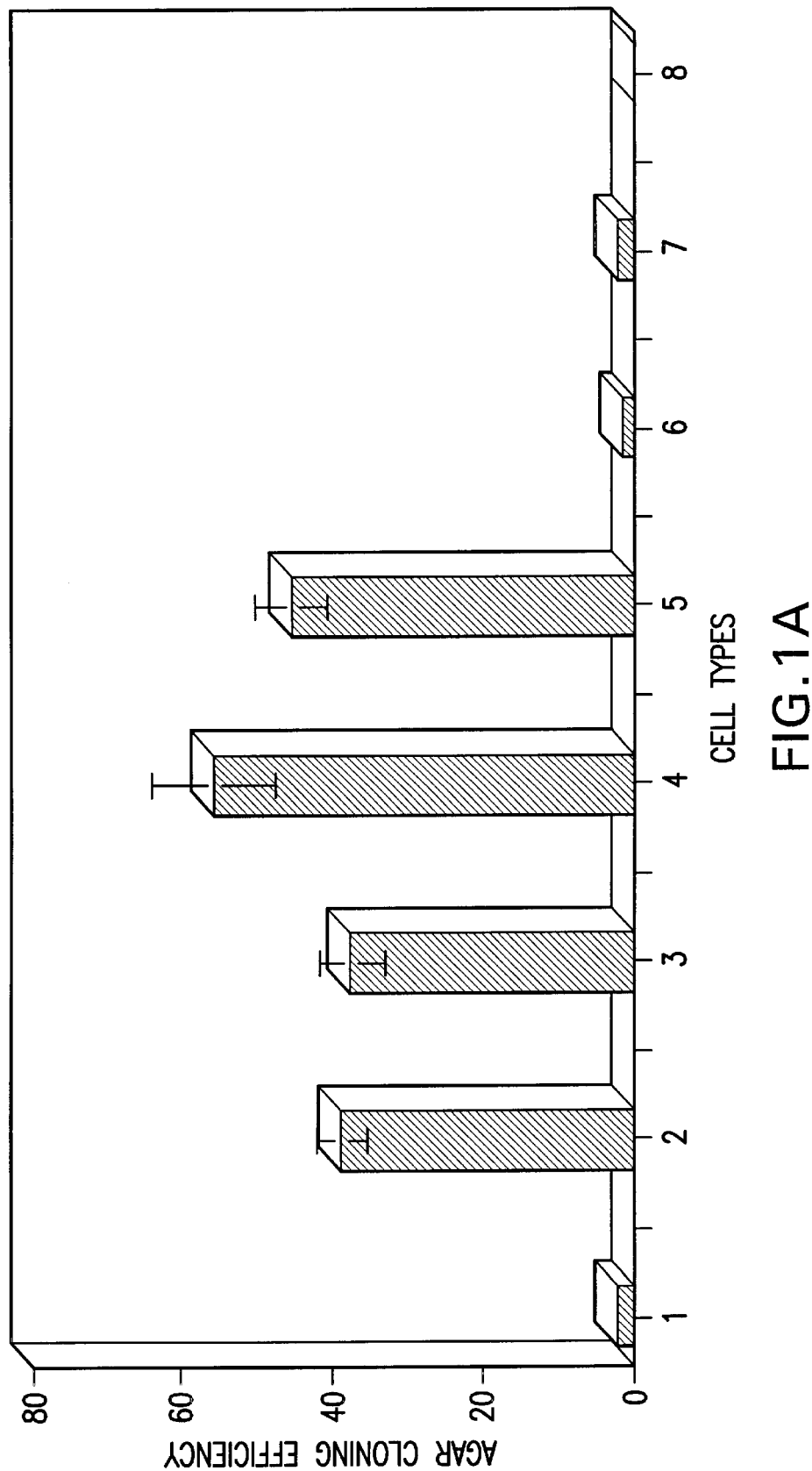

-1777

| | |
|---|---|
| ACATGGGCACGCGTGGTCGACGGCCCCGGGCTGGCTGGGCAACACGGGTTCAGCCCAGGTTTCATAGTAAGTTCCAGACAC | -1697 |
| TCCTGGAAAAACAATACAGGTCCCTGACAAAAGAAAAAACAAAACAAAGGAAACAGAAACATGCGTTTTTAAAAAAGAAG | -1617 |
| GAGGAGACTCCATGAAGGCAGGCCTTGGGTGGGGTCACTGCTTCTCTGTACACAGGAGGAGAATTGCCAAGATCTTCCGG | -1537 |
| ACAGTGTGGACTATACTGTAAGACCCTCTCAATACAGACAGACTGGACAGGCATAGTGACACATGCCTTTAATGCCTGCA | -1457 |
| GTACTCAGGAGGAGGTGGCAGGTGGAACGGCTGTTCTTTGAGGTTCAAGACCAGCGTGGACTACAGAGTGAGTTCCAGGA | -1377 |
| CAGGCAGGGCTACACAGAAAAATCCTGTCTGAAAACAAAACAAAACCCAGACAGACACACCAAAAACAGCCAAGGGACCA | -1297 |
| GAGAGATGGGTCAGGGCCTAATCACTTGCTACTCTTTGCAGAGGACCCAAATTTAGTTCCTATAACCCTCCATGAGAAGC | -1217 |
| TTCACAATTGTCTCTAACTCAATTCCACCCGTGTTCCGACCTCCCATATGCACCAGACATGTTATACTCACACATACGCA | -1137 |
| CAAACACACACACACACACACACACACACACACACACACACACACACACACGGAAAACATATAAAATAAAGATTTAAAAA | -1057 |
| ATCTTTTTCTTTTGGCCGGGGTGTGTGGGAGAGCATCTGAGCCATCTCACCAGCCCAGGGTGCACGTCTTTTTCTTTTTT | - 977 |
| TCGGAGCTGGGGACCGAACCCAGAGCCTTGTGCTTGCTAGGCAAGTGCTCTACCACTGAGCTAAATCCCCAACCCCGGAG | - 897 |
| CACGTCTTTAATCCCAGAATCAGGAGGTAGAGGTAATGAGATCCCAGTGAGCCCAAGGTCAGCCGAGTCTACAAAGTGAG | - 817 |
| TTCCAGGACAGCCAGAACTAATCTTGGAAAAACAAACAAGGGCTGGTGAGGTGGTTCAGTAGTTAAGAACACTGGCTGCT | - 737 |
| CTTCCAGAGGTCCTGAGTTCATTCTCAGTAACCACATGGTGGGGATCTGATGCCTGTTCTGGCATGCAGATATACATGCA | - 657 |
| GATAGTGCACTCCTACATTTAAAAAAAAAAGACATAAATAATATTTTAAAACATTGGGCGTTTTGTCTTCTAATAAAACT | - 577 |
| TCACTGCTATCTTCTAATAAAAATTCACTGCTAGCCGCGGGGTGTGGTGC CCCCATACCTTAATCCCAACAACTTGAGA | - 497 |
| GGCAGAGGCAGGCGGACCTTTGAGTTTGAAGCTAGCCTGGTCTACAGAGTGAGTTCAAGATAGCCACGGATAGTCAGAAA | - 417 |
| GTCCTGTTTCGAACCTCTCCCCAACCAAATCACTCCTGTAATCCCAGCACTCTGGAGGCAGTAGCAGGTTAGTCCCTGCT | - 337 |
| TCTCAGAGAGAGGAGAGAGAGAGAGAGAGAGGAGACACACACACACAGAGACAGAGAGGAGAGAGAAAGAGAAAGAGA | - 257 |
| ATGGGACAGCATGTGACTGCCTGATGAAGTTGGCGTGCTTGCTCAAAAGTTCTGCGAGATTGACGGCTCTCTGGATTTGA | - 177 |
| GCCAAGGACACGCCTGGGAAGCCACGGTGACCTCACAAGGCCCGGAATCTCCGCGAGAATTTCAGTGTTGTTTTCCTCTC | - 97 |
| TCCACCTTTCTCAGGGACTTCCGAAACTCCGCCTCTCCGGTGACGTCAGCATAGCGCTGCGTCAGACTATAAACTCCCGG | - 17 |
| GTGATCGTGTTGGCGCAGATTGACTCAGTTCGCAGCTTGTGGAAGATTACATGCGAGACCCCGCGCGACTCCGCATCCCT | + 64 |
| TTGCCGGGACAGCCTTTGCGACAGCCCGTGAGACATCACGTCCCCGAGCCCCACGCCTGAGGGCGACATGAACGCGCTGG | + 144 |
| CCTTGAGAGCAATCCGGACCCACGATCGCTTTTGGCAAACCGAACCGGAC + 194 | |

FIG.2

SEQUENCE LISTING

```
<160> NUMBER OF SEQ ID NOS: 12

<210> SEQ ID NO 1
<211> LENGTH: 1970
<212> TYPE: DNA
<213> ORGANISM: Rattus norvegicus
<220> FEATURE:
<221> NAME/KEY: promoter
<222> LOCATION: (1507)...(1970)
<223> OTHER INFORMATION: PEG-3 Promoter (corresponds to -270 to +194 of
      Figure 2)
<220> FEATURE:
<221> NAME/KEY: protein_bind
<222> LOCATION: (1672)...(1677)
<223> OTHER INFORMATION: PEA3 protein binding site
<220> FEATURE:
<221> NAME/KEY: TATA_signal
<222> LOCATION: (1748)...(1753)
<220> FEATURE:
<221> NAME/KEY: misc_feature
<222> LOCATION: (1777)...(1777)
<223> OTHER INFORMATION: RNA cap site (corresponds to +1 of Figure 2)
<220> FEATURE:
<221> NAME/KEY: protein_bind
<222> LOCATION: (1781)...(1787)
<223> OTHER INFORMATION: AP1 protein binding site
```

-continued

```
<400> SEQUENCE: 1
acatgggcac gcgtggtcga cggcccgggc tggctgggca cacggggttc agcccaggtt      60
tcatagtaag ttccagacac tcctggaaaa acaatacagg tccctgacaa agaaaaaaac     120
aaaacaaagg aaacagaaac atgcgttttt aaaaagaag gaggagactc catgaaggca      180
ggccttgggt ggggtcactg cttctctgta cacaggagga gaattgccaa gatcttccgg     240
acagtgtgga ctatactgta agaccctctc aatacagaca gactggacag gcatagtgac     300
acatgccttt aatgcctgca gtactcagga ggaggtggca ggtggaacgg ctgttctttg     360
aggttcaaga ccagcgtgga ctacagagtg agttccagga caggcagggc tacacagaaa     420
aatcctgtct gaaaacaaaa caaaacccag acagacacac caaaaacagc caagggacca     480
gagagatggg tcagggccta atcacttgct actctttgca gaggacccaa atttagttcc     540
tataaccctc catgagaagc ttcacaattg tctctaactc aattccaccc gtgttccgac     600
ctcccatatg caccagacat gttatactca acatacgca caaacacaca cacacacaca     660
cacacacaca cacacacaca cacacacaca cggaaaacat ataaaataaa gatttaaaaa     720
atctttttct tttggccggg gtgtgtggga gagcatctga gccatctcac cagcccaggg     780
tgcacgtctt tttctttttt tcggagctgg ggaccgaacc cagagccttg tgcttgctag     840
gcaagtgctc taccactgag ctaaatcccc aaccccggag cacgtcttta atcccagaat     900
caggaggtag aggtaatgag atcccagtga gcccaaggtc agccgagtct acaaagtgag     960
ttccaggaca gccagaacta atcttggaaa acaaacaag gctggtgag gtggttcagt     1020 agttaagaac actggctgct cttccagagg tcctgagttc attctcagta accacatggt     1080
ggggatctga tgcctgttct ggcatgcaga tatacatgca gatagtgcac tcctacattt     1140
aaaaaaaaaa gacataaata atattttaaa acattgggcg ttttgtcttc taataaaact     1200
tcactgctat cttctaataa aaattcactg ctagccgcgg ggtgtggtgc ccccatacct     1260
ttaatcccaa caacttgaga ggcagaggca ggcggacctt tgagtttgaa gctagcctgg     1320
tctacagagt gagttcaaga tagccacgga tagtcagaaa gtcctgtttc gaacctctcc     1380
ccaaccaaat cactcctgta atcccagcac tctggaggca gtagcaggtt agtccctgct     1440
tctcagagag aggagagaga gagagagaga gaggagacac acacacacag agacagagag     1500
gagagagaaa gagaaagaga atgggacagc atgtgactgc ctgatgaagt tggcgtgctt     1560
gctcaaaagt tctgcgagat tgacggctct ctggatttga gccaaggaca cgcctgggaa     1620
gccacggtga cctcacaagg cccggaatct ccgcgagaat ttcagtgttg ttttcctctc     1680
tccacctttc tcagggactt ccgaaactcc gcctctccgg tgacgtcagc atagcgctgc     1740
gtcagactat aaactcccgg gtgatcgtgt tggcgcagat tgactcagtt cgcagcttgt     1800
ggaagattac atgcgagacc ccgcgcgact ccgcatccct ttgccgggac agcctttgcg     1860
acagcccgtg agacatcacg tccccgagcc ccacgcctga gggcgacatg aacgcgctgg     1920
ccttgagagc aatccggacc cacgatcgct tttggcaaac cgaaccggac                1970
```

<210> SEQ ID NO 2
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 2
gatctagggt gttgtgagag gatcggag                                        28

```
<210> SEQ ID NO 3
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 3
tcggtttgcc aaaagcgatc gtggg                                  25

<210> SEQ ID NO 4
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 4
ggcaaaggga tgcggagtcg cgcgggtctc gcatg                       35

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
cgcagattga ctcagttcgc                                        20

<210> SEQ ID NO 6
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 6
gtctaactga gtcaagcg                                          18

<210> SEQ ID NO 7
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 7
cgcagataaa ctagttcgc                                         19

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
gcgtctattt gatgcaagcg                                        20

<210> SEQ ID NO 9
<211> LENGTH: 20
<212> TYPE: DNA
<213> ORGANISM: Artificial Sequence
<220> FEATURE:
```

```
<223> OTHER INFORMATION: synthetic oligonucleotide

<400> SEQUENCE: 9
gtgttgtttt cctctctcca                                            20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10
cacaacaaaa ggagagaggt                                            20

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
gtgttgttcc catctctcca                                            20

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
cacaacaagg gtagagaggt                                            20
```

NUCLEIC ACIDS COMPRISING REGIONS OF THE RAT PEG-3 PROMOTER THAT DISPLAY ELEVATED EXPRESSION IN HUMAN CANCER CELLS AND USES THEREOF

This application is a continuation-in-part application of U.S. patent application Ser. No. 09/052,753, filed Mar. 31, 1998, now U.S. Pat. No. 6,472,320 which is a continuation-in-part application of International Application No. PCT/US98/05793, filed Mar. 20, 1998.

The invention disclosed herein was made with Government support under National Cancer Institute Grant Nos. CA35675 and CA74468 from the U.S. Department of Health and Human Services. Accordingly, the U.S. Government has certain rights in this invention.

BACKGROUND OF THE INVENTION

Throughout this application, various publications are referenced by author and date within the text. Full citations for these publications may be found listed alphabetically at the end of the specification immediately preceding the claims. All patents, patent applications and publications cited herein, whether supra or infra, are hereby incorporated by reference in their entirety. The disclosures of these publications in their entireties are hereby incorporated by reference into this application in order to more fully describe the state of the art as known to those skilled therein as of the date of the invention described and claimed herein.

SUMMARY OF THE INVENTION

This invention provides for an isolated nucleic acid comprising a PEG-3 promoter comprising the nucleotide sequence beginning with the guanosine (G) at position −270 and ending with the cytosine (C) at position +194 of FIG. 2 (nucleotides 1507–1970 of SEQ ID NO:1). The invention also provides for a method for identifying an agent which modulates PEG-3 promoter activity in a cell which comprises: (a) contacting the cell with the agent wherein the cell comprises a nucleic acid comprising a PEG-3 promoter operatively linked to a reporter gene; (b) measuring the level of reporter gene expression in the cell; and (c) comparing the expression level measured in step (b) with the reporter gene expression level measured in an identical cell in the absence of the agent, wherein a lower expression level measured in the presence of the agent is indicative of an agent that inhibits PEG-3 promoter activity and wherein a higher expression level measured in the presence of the agent is indicative of an agent that enhances PEG-3 promoter activity, thereby identifying an agent which modulates PEG-3 promoter activity in the cell. The invention provides a method for treating cancer in a subject which comprises administering a nucleic acid comprising a PEG-3 promoter operatively linked to a gene-of-interest wherein the gene of interest is selectively expressed in cancerous cells in the subject and such expression results in growth suppression or death of the cancerous cells, thereby treating cancer in the subject.

BRIEF DESCRIPTION OF THE FIGURES

FIGS. 1A–1C: Anchorage independent growth and PEG-3 mRNA and protein expression in normal, adenovirus-transformed and somatic cell hybrid rodent cells. (FIG. 1A) Anchorage-independent growth assays were determined by plating $5 \times 10^3$ or $1 \times 10^4$ cells in 0.4% agar containing medium on top of a 0.8% agar medium containing base layer. After two weeks growth, colonies $\geq 0.1$ mm were enumerated using an inverted microscope. The results are the average of 3 independent experiments using triplicate samples per experiment±SD. (FIG. 1B) PEG3 mRNA levels were determined by electrophoresing 15 µg of total cellular RNA in a 1.2% agarose gel. RNA was transferred to nylon membranes and hybridized with a $^{32}$P-labeled PEG-3 cDNA probe, the blot was stripped and then rehybridized with a $^{32}$P-labeled GAPDH probe. (FIG. 1C) PEG-3 and actin protein levels were determined by Western blotting. Ten µg of protein from each cell type was loaded onto a 10% denatured polyacrylamide gel and electrophoreised for 3 hr followed by transfer to a nitrocellulose membrane. PEG-3 protein was detected using Anti-PEG-3 antibody and actin protein was detected by Ant-Actin antibody. Lane designation: 1 E11; 2 E11-NMT; 3 E11-Ha-ras R12; 4; E11-NMT× CREF R1; 5 E11-NMT×CREF R2; 6 E11-NMT×CREF F1; 7 E11-NMT×CREF F2; and 8 CREF.

FIG. 2: Sequence of the 2.0-kb PEG-3 promoter. (SEQ ID NO:1) This fragment was identified by 5' DNA walking as described in Materials and Methods. The location of PEA3 and AP1 elements and the TATA boxes are indicated.

(FIG. 5A) Schematic representation of deletion mutants of the PEG-Prom. Mutants were constructed as described in Materials and Methods. (FIG. 5B) Fold activation of the FL-PEG-Prom (lane 1) and the various PEG-Prom deletion mutants (lanes 2 to 11) in E11 and E11-NMT cells. Fold activation compares the FL-PEG-Prom and various deletion mutants of PEG-Prom versus the specific PEG-Prom deletion construct (deleted at position −40) which contains the TATA box and AP1 element. This deletion construct is given the arbitrary value of one. Promoter-luciferase assays were performed as described in Materials and Methods.

(FIG. 6A) Schematic representation of the specific mutations in the PEG-Prom analyzed for activity in E11 and E11-NMT cells. Point mutations were made using a site-specific mutagenesis as described in Materials and Methods. (FIG. 6B) Fold activation of the various PEG-Prom mutants in E11 and E11-NMT cells. Fold activation compares the PEG-Prom mutant (deleted at position −118) and additional mutants containing point or deletion mutations effecting the PEA3 and AP1 sites and/or the TATA box region versus the specific PEG-Prom deletion construct (deleted at position −40) which contains a wild-type TATA box and AP1 element. This latter deletion construct is given the arbitrary value of one. Promoterluciferase assays were performed as described in Materials and Methods.

Figure 7A:
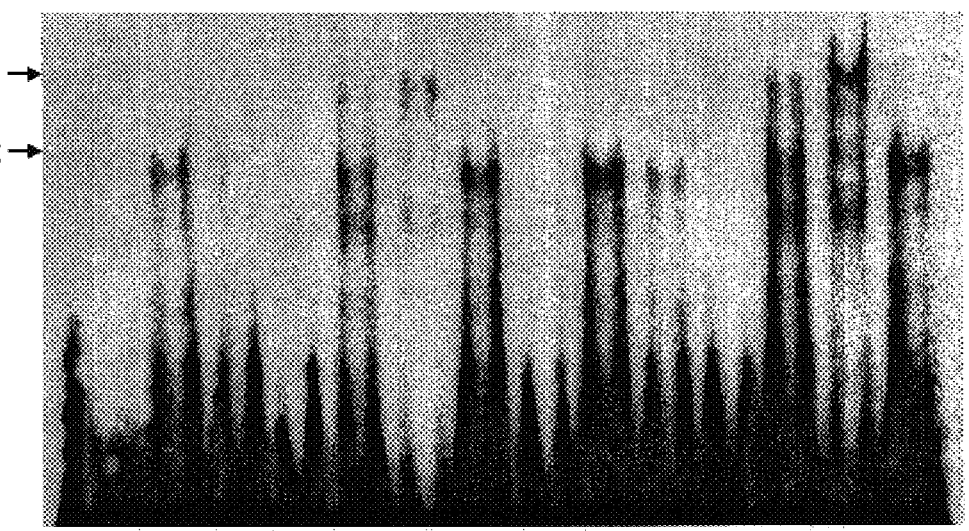
Figure 7B:
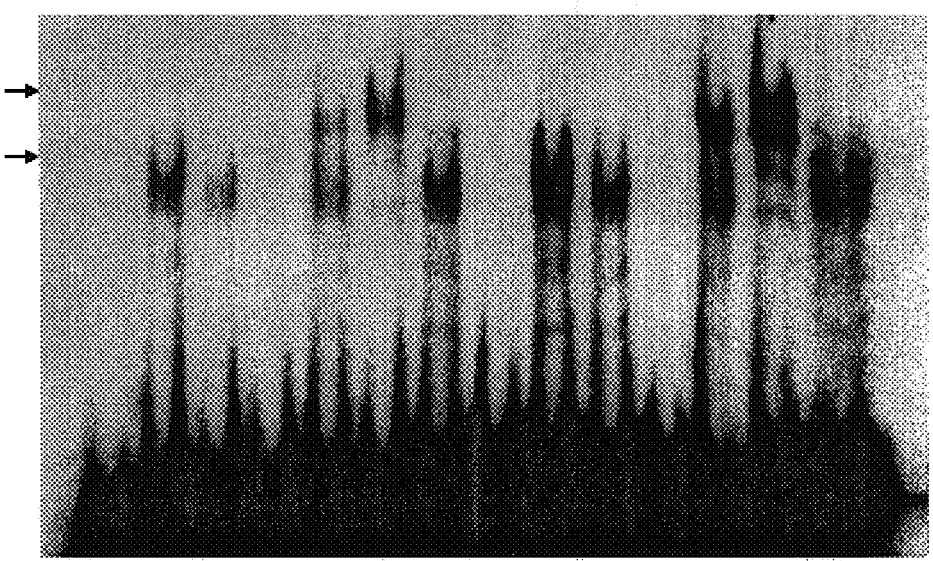

FIGS. 7A–7B: Analysis of nuclear protein binding to AP1 and PEA3 elements by EMSA. (FIG. 7A) AP1 and (FIG. 7B) PEA3 nucleoprotein complexes in E11 and E11-NMT cells were identified using EMSA. Nuclear extracts were prepared from the two cell types and incubated with an AP1 or PEA3 probe labeled with $^{32}$P using $\gamma^{32}$P-ATP and T4 DNA kinase. The reaction mixture was electrophoresied in a 5% non-denatured polyacrylamide gel as described in Materials and Methods. Arrow 1 indicates supershifted AP1 (FIG. 7A) or PEA3 (FIG. 7B) DNA-protein-antibody complexes and arrow 2 indicates the AP1 (FIG. 7A) or PEA3 (FIG. 7B) DNA protein complexes in E11 and E11-NMT cells. All of the samples contain nuclear extracts from either E11 or E11-NMT cells. Mut-oligo sample contains a mutated AP1 (FIG. 7A) or PEA3 (FIG. 7B) oligonucleotide. WT-Oligo sample contains a wild-type AP1 (FIG. 7A) or PEA3 (FIG. 7B) oligonucleotide. Competitor refers to the presence of a 10× (10-fold) or 100× (100-fold) molar excess of unlabeled competitor oligonucleotides. cjun-Ab (FIG. 7A) and PEA3-Ab (FIG. 7B) samples contain 1 or 5 $\mu$g of the respective antibody. Actin-Ab sample contains 5 $\mu$g of anti-actin antibody.

Figure 8:
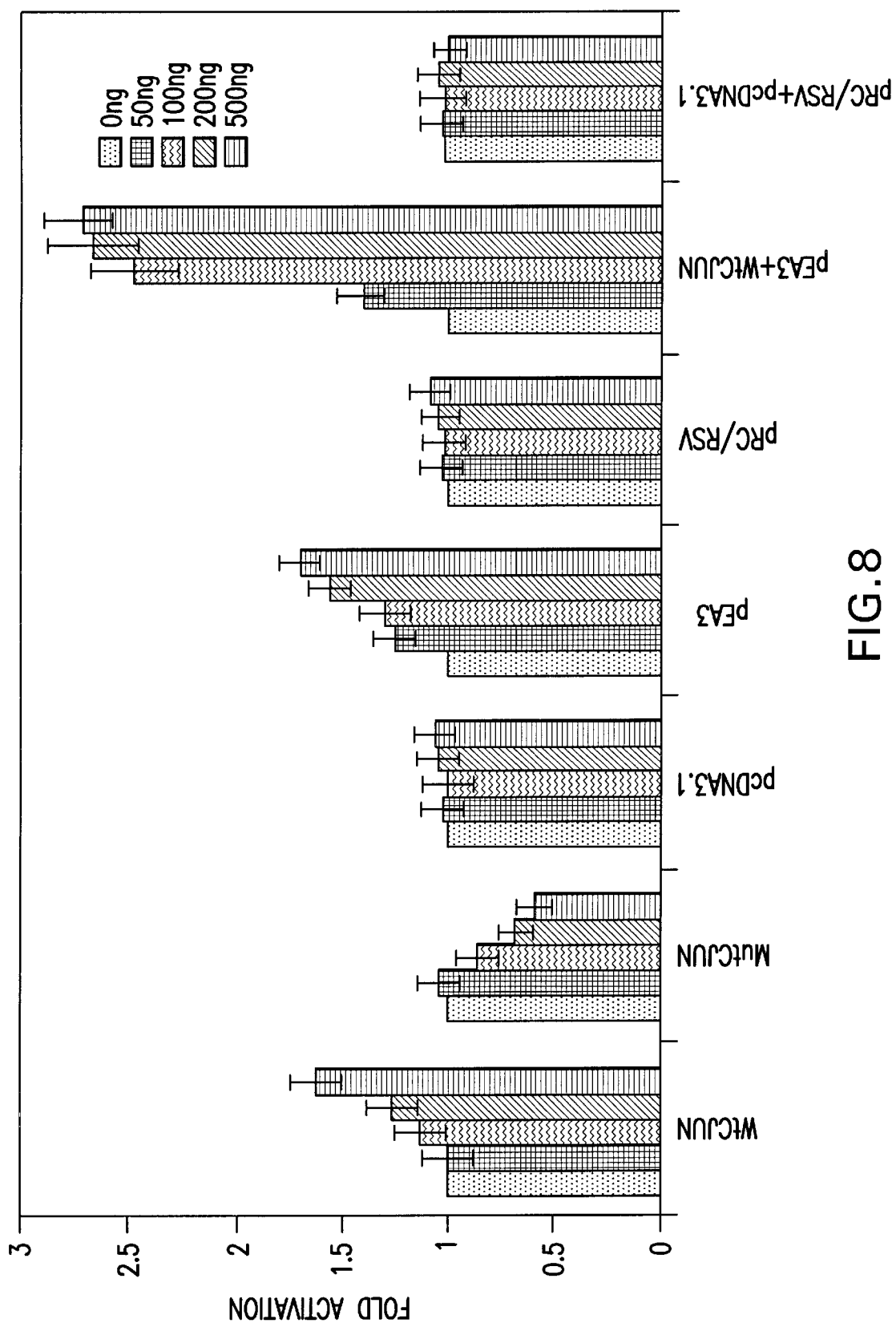

FIG. 8: Effect of ectopic expression of cJun (AP1) and PEA3, alone and in combination, on FL-PEG-Prom activity in E11 cells. Various amounts (50 to 500 ng) of wild-type cJun (wtcjun), mutant TAM67 cJun (mutcjun), pcDNA3.1 (control vector), PEA3 (pEA3), pRC/RSV (control vector), a combination of PEA3 and wild-type cJun (pEA3+wtcjun) or a combination of control vectors (pRC/RSV+pcDNA3.1) were transfected with 5 $\mu$g of pGL3/PEG-Prom and 1 $\mu$g of pSV-$\beta$-galactosidase vector into E11 cells. The results represent average fold activation in comparison with vector transfected E11 cells of 2 independent experiments with triplicate samples per experiment±SD.

DETAILED DESCRIPTION OF THE INVENTION

The following several of the abbreviations used herein: progression elevated gene-3 (PEG-3); rat embryonic cells (RE cells); PEG-promoter (PEG-Prom); kilobases (kb). Throughout this application, references to specific nucleotides are to nucleotides present on the coding strand of the nucleic acid. The following standard abbreviations are used throughout the specification to indicate specific nucleotides:

C=cytosine A=adenosine

T=thymidine G=guanosine

This invention provides for an isolated nucleic acid comprising a PEG-3 promoter comprising the nucleotide sequence beginning with the guanosine (G) at position −270 and ending with the cytosine (C) at position +194 of FIG. 2 (nucleotides 1507–1970 of SEQ ID NO:1).

The invention also provides an isolated nucleic acid comprising a fragment of the nucleotide sequence of nucleotides −270 to +194 of FIG. 2 (residues 1507–1970 of SEQ ID NO:1) which is at least 15 nucleotides in length.

In one embodiment, the nucleic acid fragment comprises
(i) a PEA3 protein binding sequence consisting of the nucleotide sequence beginning with the thymidine (T) at position −105 and ending with the thymidine (T) at position −100 of FIG. 2 (nucleotides 1672–1677 of SEQ ID NO:1),
(ii) a TATA sequence consisting of the nucleotide sequence beginning with the thymidine (T) at position −29 and ending with the adenosine (A) at position −24 of FIG. 2 (nucleotides 1748–1753 of SEQ ID NO:1), or
(iii) an AP1 protein binding sequence consisting of the nucleotide sequence beginning with the thymidine (T) at position +5 and ending with the adenosine (A) at position +11 of the nucleotide sequence shown in FIG. 2 (nucleotides 1781–1787 of SEQ ID NO:1).

In another embodiment, the nucleic acid comprises at least two of the nucleotide sequences (i) to (iii) listed above.

In another embodiment, the nucleic acid comprises the three nucleotide sequences (i) to (iii) listed above.

In another embodiment, the fragment has promoter activity.

In another embodiment, the fragment is operably linked to a gene of interest. In another embodiment, the gene of interest is a reporter gene.

In another embodiment, the reporter gene encodes beta-galactosidase, luciferase, chloramphenicol transferase or alkaline phosphatase.

In another embodiment, the gene of interest is a tumor suppressor gene, a gene whose expression causes apoptosis of a cell, or a cytotoxic gene.

The invention provides for a vector comprising at least one of the nucleic acids described herein. The invention also provides for a host cell comprising this vector.

In another embodiment, the host cell is a tumor cell. In another embodiment, the tumor cell is a melanoma cell, a neuroblastoma cell, a cervical cancer cell, a breast cancer cell, a lung cancer cell, a prostate cancer cell, a colon cancer cell or a glioblastoma multiforme cell.

The invention also provides for a method for identifying an agent which modulates PEG-3 promoter activity in a cell which comprises: (a) contacting the cell with the agent wherein the cell comprises a nucleic acid comprising a PEG-3 promoter operatively linked to a reporter gene; (b) measuring the level of reporter gene expression in the cell; and (c) comparing the expression level measured in step (b) with the reporter gene expression level measured in an identical cell in the absence of the agent, wherein a lower expression level measured in the presence of the agent is indicative of an agent that inhibits PEG-3 promoter activity and wherein a higher expression level measured in the presence of the agent is indicative of an agent that enhances PEG-3 promoter activity, thereby identifying an agent which modulates PEG-3 promoter activity in the cell.

In another embodiment, the cell is a melanoma cell, a neuroblastoma cell, a cervical cancer cell, a breast cancer cell, a lung cancer cell a prostate cancer cell, a colon cancer cell or a glioblastoma multiforme cell.

In another embodiment, the agent comprises a molecule having a molecular weight of about 7 kilodaltons or less.

In another embodiment, the agent is an antisense nucleic acid comprising a nucleotide sequence complementary to at least a portion of the sequence shown in SEQ ID NO: 1 and is at least 15 nucleotides in length.

In another embodiment, the agent is a DNA molecule, a carbohydrate, a glycoprotein, a transcription factor protein or a double-stranded RNA molecule.

In another embodiment, the agent is a synthetic nucleotide sequence, a peptidomimetic, or an organic molecule having a molecular weight from 0.1 kilodaltons to 10 kilodaltons.

In another embodiment, the reporter gene encodes beta-galactosidase, luciferase, chloramphenicol transferase or alkaline phosphatase.

In another embodiment, expression of PEG-3 promoter activity measured is equal to or greater than a 2.5 to 3.5 fold increase or decrease.

The invention provides for a method for treating cancer in a subject which comprises administering a nucleic acid comprising a PEG-3 promoter operatively linked to a gene-of-interest wherein the gene-of-interest is selectively expressed in cancerous cells in the subject and such expression results in growth suppression or death of the cancerous cells, thereby treating cancer in the subject.

In one embodiment of this invention, the nucleic acid consists essentially of (i) a PEA3 protein binding sequence consisting of the nucleotide sequence beginning with the thymidine (T) at position −105 and ending with the thymidine (T) at position −100 of FIG. 2, (ii) a TATA sequence consisting of the nucleotide sequence beginning with the thymidine (T) at position −29 and ending with the adenosine (A) at position −24 of FIG. 2, and (iii) an AP1 protein binding sequence consisting of the nucleotide sequence beginning with the thymidine (T) at position +5 and ending with the adenosine (A) at position +11 of the nucleotide sequence shown in FIG. 2.

In another embodiment, the nucleic acid has a sequence complementary to at least a portion of SEQ ID NO: 1 of at least 25 nucleotides in length.

In another embodiment, the cancer is melanoma, neuroblastoma, astrocytoma, glioblastoma multiforme, cervical cancer, breast cancer, colon cancer, prostate cancer, osteoscarcoma or chrondosarcoma.

In another embodiment, the administering is carried out via injection, oral administration, topical administration, adenovirus infection, liposome-mediated transfer, topical application to the cells of the subject, or microinjection.

In another embodiment, the subject is a mammal. In another embodiment, the mammal is a human. In another embodiment, the gene of interest is an gene whose expression causes apoptosis of a cell.

In another embodiment, the gene comprises an Mda-7 gene or a p53 gene. In another embodiment, the gene of interest is a tumor suppressor gene. In another embodiment, the suppressor gene is mda-7. In another embodiment, the gene of interest is a cytotoxic gene. In another embodiment, expression of the cytotoxic gene causes cell death.

In another embodiment, the cytotoxic gene is selected from the group consisting of HSV-TK, p21, p27, and p10.

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, Molecular Cloning: A Laboratory Manual, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I–IV (D. M. Weir and C. C. Blackwell eds., 1986, Blackwell Scientific Publications).

As used in this specification and the appended claims, the singular forms "a," "an" and "the" include plural references unless the content clearly dictates otherwise.

The invention provides for a host cell comprising the recombinant expression construct as described herein.

In another embodiment of the invention, the host cell is stably transformed with the recombinant expression construct described herein. In another embodiment of the invention, the host cell is a tumor cell.

In another embodiment of the invention, the host cell is a melanocyte. In another embodiment of the invention, the cell is an immortalized cell.

In another embodiment of the invention, the tumor cell is a melanoma cell, a neuroblastoma cell, an astrocytoma cell, a glioblastomoa multifore cell, a cerival cancer cell, a breast cancer cell, a lung cancer cell or a prostate cancer cell.

The invention provides for a method for expressing foreign DNA in a host cell comprising: introducing into the host cell a gene transfer vector comprising a PEG-3 promoter nucleotide sequence operably linked to a foreign DNA encoding a desired polypeptide or RNA, wherein said foreign DNA is expressed.

In another embodiment of the invention, the gene transfer vector encodes and expresses a reporter molecule.

In another embodiment of the invention, the reporter molecule is selected from the group consisting of beta-galactosidase, luciferase and chloramphenicol acetyltransferase.

In another embodiment of the invention, the "introducing" is carried out by a means selected from the group consisting of adenovirus infection, liposome-mediated transfer, topical application to the cell, and microinjection.

In another embodiment of the invention, the cancer is melanoma, neuroblastoma, astrocytoma, glioblastoma multiforme, cervical cancer, breast cancer, colon cancer, prostate cancer, osteoscarcoma, or chrondosarcoma.

In another embodiment of the invention, the cancer is a cancer of the central nervous system of the subject.

In another embodiment of the invention, the administering is carried out via injection, oral administration, or topical administration.

In another embodiment of the invention, the carrier is an aqueous carrier, a liposome, or a lipid carrier.

Definition

As used herein "therapeutic gene" means DNA encoding an amino acid sequence corresponding to a functional protein capable of exerting a therapeutic effect on cancer cells or having a regulatory effect on the expression of a gene which functions in cells.

As used herein "nucleic acid molecule" includes both DNA and RNA and, unless otherwise specified, includes both double-stranded and single-stranded nucleic acids. Also included are hybrids such as DNA-RNA hybrids. Reference to a nucleic acid sequence can also include modified bases as long as the modification does not significantly interfere either with binding of a ligand such as a protein by the nucleic acid or Watson-Crick base pairing.

As used herein "enhancer element" is a nucleotide sequence that increases the rate of transcription of the therapeutic genes or genes of interest but does not have promoter activity. An enhancer can be moved upstream, downstream, and to the other side of a promoter without significant loss of activity.

Two DNA or polypeptide sequences are "substantially homologous" when at least about 80% (preferably at least about 90%, and most preferably at least about 95%–99%) of the nucleotides or amino acids match over a defined length of the molecule. As used herein, "substantially homologous" also refers to sequences showing identity (100% identical sequence) to the specified DNA or polypeptide sequence. DNA sequences that are substantially homologous can be identified in a Southern hybridization, experiment under, for example, stringent conditions, as defined for that particular system. Defining appropriate hybridization conditions is within the skill of the art. See, e.g., Sambrook et al., supra; DNA Cloning, vols I & II, supra; Nucleic Acid Hybridization, supra.

A sequence "functionally equivalent" to a PEG-3 promoter sequence is one which functions in the same manner as the PEG-3 promoter sequence. Thus, a promoter sequence "functionally equivalent" to the PEG-3 promoter described herein is one which is capable of directing transcription of a downstream coding sequence in substantially similar timeframes of expression and in substantially similar amounts and with substantially similar tissue specificity as the PEG-3 promoter sequence.

A DNA "coding sequence" or a "nucleotide sequence encoding" a particular protein, is a DNA sequence which is transcribed and translated into a polypeptide in vivo or in vitro when placed under the control of appropriate regulatory sequences. The boundaries of the coding sequence are determined by a start codon at the 5'-(amino) terminus and a translation stop codon at the 3'-(carboxy) terminus. A coding sequence can include, but is not limited to, procaryotic sequences, cDNA from eucaryotic mRNA, genomic DNA sequences from eucaryotic (e.g., mammalian) sources, viral RNA or DNA, and even synthetic nucleotide sequences. A transcription termination sequence will usually be located 3' to the coding sequence.

DNA "control sequences" refers collectively to promoter sequences, polyadenylation signals, transcription termination sequences, upstream regulatory domains, enhancers, and the like, untranslated regions, including 5'-UTRs (untranslated regions) and 3'-UTRs, which collectively provide for the transcription and translation of a coding sequence in a host cell.

"Operably linked" refers to an arrangement of nucleotide sequence elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A control sequence "directs the transcription" of a coding sequence in a cell when RNA polymerase will bind the promoter sequence and transcribe the coding sequence into mRNA, which is then translated into the polypeptide encoded by the coding sequence.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. In eucaryotic cells, a stably transformed cell is generally one in which the exogenous DNA has become integrated into the chromosome so that it is inherited by daughter cells through chromosome replication, or one which includes stably maintained extra-chromosomal plasmids. This stability is demonstrated by the ability of the eucaryotic cell to establish cell lines or clones comprised of a population of daughter cells containing the exogenous DNA.

A "heterologous" region of a DNA construct is an identifiable segment of DNA within or attached to another DNA molecule that is not found in association with the other molecule in nature. For example, a sequence encoding a protein other than a PEG-3 protein is considered a heterologous sequence when linked to a PEG-3 promoter. Another example of a heterologous coding sequence is a construct where the coding sequence itself is not found in nature (e.g., synthetic sequences having codons different from the native gene). Likewise, a chimeric sequence, comprising a heterologous gene linked to a PEG-3 promoter, will be considered heterologous since such chimeric constructs are not normally found in nature. Allelic variation or naturally occurring mutational events do not give rise to a heterologous region of DNA, as used herein.

Vectors

Especially preferred are virus based vectors. In the case of eukaryotic cells, retrovirus or adenovirus based vectors are preferred. Such vectors contain all or a part of a viral genome, such as long term repeats ("LTRs"), promoters (e.g., CMV promoters, SV40 promoter, RSV promoter), enhancers, and so forth. When the host cell is a prokaryote, bacterial viruses, or phages, are preferred. Exemplary of such vectors are vectors based upon, e.g., lambda phage. In any case, the vector may comprise elements of more than one virus.

The resulting vectors are transfected or transformed into a host cell, which may be eukaryotic or prokaryotic.

The gene transfer vector of the present invention may additionally comprise a gene encoding a marker or reporter molecule to more easily trace expression of the vector.

The particular reporter molecule which can be employed in the present invention is not critical thereto. Examples of such reporter molecules which can be employed in the present invention are well-known in the art and include beta-galactosidase (Fowler et al, Proc. Natl. Acad. Sci., USA, 74:1507 (1977)), luciferase (Tu et al, Biochem., 14:1970 (1975)), and chloramphenicol acetyltransferase (Gorman et al, Mol. Cell Biol., 2:1044–1051 (1982)).

The gene transfer vector may contain more than one gene encoding the same or different foreign polypeptides or RNAs.

The gene transfer vector may be any construct which is able to replicate within a host cell and includes plasmids, DNA viruses, retroviruses, as well as isolated nucleotide molecules. Liposome-mediated transfer of the gene transfer vector may also be carried out in the present invention.

Examples of such plasmids which can be employed in the present invention include pGL3-based plasmids (Promega™). An example of such DNA viruses which can be employed in the present invention are adenoviruses.

Adenoviruses have attracted increasing attention as expression vectors, especially for human gene therapy (Berkner, Curr. Top. Microbiol. Immunol., 158:39–66 (1992)).

Examples of such adenovirus serotypes which can be employed in the present invention are well-known in the art and include more than 40 different human adenoviruses, e.g., Ad12 (subgenus A), Ad3 and Ad7 (Subgenus B), Ad2 and Ad5 (Subgenus C), Ad8 (Subgenus D), Ad4 (Subgenus E), Ad40 (Subgenus F) (Wigand et al, In: Adenovirus DNA, Doerfler, Ed., Martinus Nijhoff Publishing, Boston, pp. 408–441 (1986)). Ad5 of subgroup C is the preferred adenovirus employed in the present invention. This is because Ad5 is a human adenovirus about which a great deal of biochemical and genetic information is known, and it has historically been used for most constructions employing adenovirus as a vector. Also, adenoviral vectors are commercially available, e.g., pCA3 (Microbix Biosystems Inc.).

Methods for producing adenovirus vectors are well-known in the art (Berkner et al, Nucleic Acids Res., 11:6003–6020 (1983); van Doren et al, Mol. Cell. Biol., 4:1653–1656 (1984); Ghosh-Choudhury et al, Biochem. Biophys. Res. Commun., 147:964–973 (1987); McGrory et al, Virol., 163:614–617 (1988); and Gluzman et al, In: Eurkaryotic Viral Vectors, Ed. Gluzman, Y. pages 187–192, Cold Spring Harbor Laboratory (1982)).

Derivative Nucleic Acid Molecules

Derivative molecules would retain the functional property of the PEG-3 promoter, namely, the molecule having such substitutions will still permit the tissue specific expression of the gene of interest. Modification is permitted so long as the derivative molecules retain its increased potency compared to PEG-3 promoter alone and its tissue specificity.

Examples of therapeutic genes include suicide genes. These are genes sequences the expression of which produces a protein or agent that inhibits melanoma tumor cell growth or induces melanoma tumor cell death. Suicide genes include genes encoding enzymes, oncogenes, tumor suppressor genes, genes encoding toxins, genes encoding cytokines, or a gene encoding oncostatin. The purpose of the therapeutic gene is to inhibit the growth of or kill skin cancer cells or produce cytokines or other cytotoxic agents which directly or indirectly inhibit the growth of or kill the cancer cell.

Suitable enzymes include thymidine kinase (TK), xanthine-guanine phosphoribosyltransferase (GPT) gene from E. coli or E. coli cytosine deaminase (CD), or hypoxanthine phosphoribosyl transferase (HPRT).

Suitable oncogenes and tumor suppressor genes include neu, EGF, ras (including H, K, and N ras), p53, Retinoblastoma tumor suppressor gene (Rb), Wilm's Tumor Gene Product, Phosphotyrosine Phosphatase (PTPase), and nm23. Suitable toxins include Pseudomonas exotoxin A and S; diphtheria toxin (DT); E. coli LT toxins, Shiga toxin, Shiga-like toxins (SLT-1, -2), ricin, abrin, supporin, and gelonin.

Suitable cytokines include interferons, GM-CSF interleukins, tumor necrosis factor (TNF) (Wong G, et al., Human GM-CSF: Molecular cloning of the complementary DNA and purification of the natural and recombinant proteins. Science 1985; 228:810); WO0323034 (1993); Horisberger M. A., et al., Cloning and sequence analyses of cDNAs for interferon-beta and virus-induced human Mx proteins reveal that they contain putative guanine nucleotide-binding sites: functional study of the corresponding gene promoter. Journal of Virology, 1990 Mar, 64(3): 1171–81; Li YP et al., Proinflammatory cytokines tumor necrosis factor-alpha and IL-6, but not IL-1, down-regulate the osteocalcin gene promoter. Journal of Immunology, Feb. 1, 1992, 148(3):788–94; Pizarro T. T., et al. Induction of TNF alpha and TNF beta gene expression in rat cardiac transplants during allograft rejection. Transplantation, 1993 Aug., 56(2):399–404). (Breviario F., et al., Interleukin-1-inducible genes in endothelial cells. Cloning of a new gene related to C-reactive protein and serum amyloid P component. Journal of Biological Chemistry, Nov. 5, 1992, 267 (31):22190–7; Espinoza-Delgado I., et al., Regulation of IL-2 receptor subunit genes in human monocytes. Differential effects of IL-2 and IFN-gamma. Journal of Immunology, Nov. 1, 1992, 149(9):2961–8; Algate P. A., et al., Regulation of the interleukin-3 (IL-3) receptor by IL-3 in the fetal liver-derived FL5.12 cell line. Blood, 1994 May 1, 83(9): 2459–68; Cluitmans F. H., et al., IL-4 down-regulates IL-2-, IL-3-, and GM-CSF-induced cytokine gene expression in peripheral blood monocytes. Annals of Hematology, 1994 June, 68(6):293–8; Lagoo, A. S., et al., IL-2, IL-4, and IFN-gamma gene expression versus secretion in superantigen-activated T cells. Distinct requirement for costimulatory signals through adhesion molecules. Journal of Immunology, Feb. 15, 1994, 152(4):1641–52; Martinez O. M., et al., IL-2 and IL-5 gene expression in response to alloantigen in liver allograft recipients and in vitro. Transplantation, 1993 May, 55(5):1159–66; Pang G, et al., GM-CSF, IL-1 alpha, IL-1 beta, IL-6, IL-8, IL-10, ICAM-1 and VCAM-1 gene expression and cytokine production in human duodenal fibroblasts stimulated with lipopolysaccharide, IL-1 alpha and TNF-alpha. Clinical and Experimental Immunology, 1994 June, 96(3):437–43; Ulich T. R., et al., Endotoxin-induced cytokine gene expression in vivo. III. IL-6 mRNA and serum protein expression and the in vivo hematologic effects of IL-6. Journal of Immunology, Apr. 1, 1991, 146(7):2316–23; Mauviel A., et al., Leukoregulin, a T cell-derived cytokine, induces IL-8 gene expression and secretion in human skin fibroblasts. Demonstration and secretion in human skin fibroblasts. Demonstration of enhanced NF-kappa B binding and NF-kappa B-driven promoter activity. Journal of Immunology, Nov. 1, 1992, 149(9):2969–76).

Growth factors include Transforming Growth Factor-. alpha. (TGF-alpha) and beta (TGF-beta), cytokine colony stimulating factors (Shimane M., et al., Molecular cloning and characterization of G-CSF induced gene cDNA. Biochemical and Biophysical Research Communications, Feb. 28, 1994, 199(1):26–32; Kay A. B., et al., Messenger RNA expression of the cytokine gene cluster, interleukin 3 (IL-3), IL-4, IL-5, and granulocyte/macrophage colony-stimulating factor, in allergen-induced late-phase cutaneous reactions in atopic subjects. Journal of Experimental Medicine, Mar. 1, 1991, 173(3):775–8; de Wit H, et al., Differential regulation of M-CSF and IL-6 gene expression in monocytic cells. British Journal of Haematology, 1994 February, 86(2): 259–64; Sprecher E., et al., Detection of IL-1 beta, TNF-alpha, and IL-6 gene transcription by the polymerase chain reaction in keratinocytes, Langerhans cells and peritoneal exudate cells during infection with herpes simplex virus-1. Archives of Virology, 1992, 126(1–4):253–69).

Preferred vectors for use in the methods of the present invention are viral including adenoviruses, retroviral, vectors, adeno-associated viral (AAV) vectors.

The viral vector selected should meet the following criteria: 1) the vector must be able to infect the tumor cells and thus viral vectors having an appropriate host range must be selected; 2) the transferred gene should be capable of persisting and being expressed in a cell for an extended period of time; and 3) the vector should be safe to the host and cause minimal cell transformation. Retroviral vectors and adenoviruses offer an efficient, useful, and presently the best-characterized means of introducing and expressing foreign genes efficiently in mammalian cells. These vectors have very broad host and cell type ranges, express genes stably and efficiently. The safety of these vectors has been proved by many research groups. In fact many are in clinical trials.

Other virus vectors that may be used for gene transfer into cells for correction of disorders include retroviruses such as Moloney murine leukemia virus (MoMuLV); papovaviruses such as JC, SV40, polyoma, adenoviruses; Epstein-Barr Virus (EBV); papilloma viruses, e.g. bovine papilloma virus type I (BPV); vaccinia and poliovirus and other human and animal viruses.

Adenoviruses have several properties that make them attractive as cloning vehicles (Bachettis et al.: Transfer of gene for thymidine kinase-deficient human cells by purified herpes simplex viral DNA. PNAS USA, 1977 74:1590; Berkner, K. L.: Development of adenovirus vectors for expression of heterologous genes. Biotechniques, 1988 6:616; Ghosh-Choudhury G., et al., Human adenovirus cloning vectors based on infectious bacterial plasmids. Gene 1986; 50:161; Hag-Ahmand Y., et al., Development of a helper-independent human adenovirus vector and its use in the transfer of the herpes simplex virus thymidine kinase gene. J Virol 1986; 57:257; Rosenfeld M., et al., Adenovirus-mediated transfer of a recombinant. alpha..sub.1—antitrypsin gene to the lung epithelium in vivo. Science 1991; 252:431).

For example, adenoviruses possess an intermediate sized genome that replicates in cellular nuclei; many serotypes are clinically innocuous; adenovirus genomes appear to be stable despite insertion of foreign genes; foreign genes appear to be maintained without loss or rearrangement; and adenoviruses can be used as high level transient expression vectors with an expression period up to 4 weeks to several months. Extensive biochemical and genetic studies suggest that it is possible to substitute up to 7–7.5 kb of heterologous sequences for native adenovirus sequences generating viable, conditional, helper-independent vectors (Kaufman R. J.; identification of the component necessary for adenovirus translational control and their utilization in cDNA expression vectors. PNAS USA, 1985 82:689).

AAV is a small human parvovirus with a single stranded DNA genome of approximately 5 kb. This virus can be propagated as an integrated provirus in several human cell types. AAV vectors have several advantage for human gene therapy. For example, they are trophic for human cells but can also infect other mammalian cells; (2) no disease has been associated with AAV in humans or other animals; (3) integrated AAV genomes appear stable in their host cells; (4) there is no evidence that integration of AAV alters expression of host genes or promoters or promotes their rearrangement; (5) introduced genes can be rescued from the host cell by infection with a helper virus such as adenovirus.

HSV-1 vector system facilitates introduction of virtually any gene into non-mitotic cells (Geller et al. an efficient deletion mutant packaging system for a defective herpes simplex virus vectors: Potential applications to human gene therapy and neuronal physiology. PNAS USA, 1990 87:8950).

Another vector for mammalian gene transfer is the bovine papilloma virus-based vector (Sarver N, et al., Bovine papilloma virus DNA: A novel eukaryotic cloning vector. Mol Cell Biol 1981; 1:486). Vaccinia and other poxvirus-based vectors provide a mammalian gene transfer system. Vaccinia virus is a large double-stranded DNA virus of 120 kilodaltons (kd) genomic size (Panicali D, et al., Construction of poxvirus as cloning vectors: Insertion of the thymidine kinase gene from herpes simplex virus into the DNA of infectious vaccine virus. Proc Natl Acad Sci USA 1982; 79:4927; Smith et al. infectious vaccinia virus recombinants that express hepatitis B virus surface antigens. Nature, 1983 302:490.)

Retroviruses are packages designed to insert viral genes into host cells (Guild B, et al., Development of retrovirus vectors useful for expressing genes in cultured murine embryonic cells and hematopoietic cells in vivo. J Virol 1988; 62:795; Hock R. A., et al., Retrovirus mediated transfer and expression of drug resistance genes in human hemopoietic progenitor cells. Nature 1986; 320:275).

The basic retrovirus consists of two identical strands of RNA packaged in a proviral protein. The core surrounded by a protective coat called the envelope, which is derived from the membrane of the previous host but modified with glycoproteins contributed by the virus.

Markers and amplifiers can also be employed in the subject expression systems. A variety of markers are known which are useful in selecting for transformed cell lines and generally comprise a gene whose expression confers a selectable phenotype on transformed cells when the cells are grown in an appropriate selective medium. Such markers for mammalian cell lines include, for example, the bacterial xanthine-guanine phosporibosyl transferase gene, which can be selected for in medium containing mycophenolic acid and xanthine (Mulligan et al. (1981) Proc. Natl. Acad. Sci. USA 78:2072–2076), and the aminoglycoside phosphotransferase gene (specifying a protein that inactivates the antibacterial action of neomycin/kanamycin derivatives), which can be selected for using medium containing neomycin derivatives such as G418 which are normally toxic to mammalian cells (Colbere-Garapin et al. (1981) J. Mol. Biol. 150:1–14). Useful markers for other eucaryotic expression systems, are well known to those of skill in the art.

Infection can be carried out in vitro or in vivo. In vitro infection of cells is performed by adding the gene transfer vectors to the cell culture medium. When infection is carried out in vivo, the solution containing the gene transfer vectors may be administered by a variety of modes, depending on the tissue which is to be infected. Examples of such modes of administration include injection of gene transfer vectors into the skin, topical application onto the skin, direct application to a surface of epithelium, or instillation into an organ (e.g., time release patch or capsule below the skin or into a tumor).

Expression can be amplified by placing an amplifiable gene, such as the mouse dihydrofolate reductase (dhfr) gene adjacent to the coding sequence. Cells can then be selected for methotrexate resistance in dhfr-deficient cells. See, e.g. Urlaub et al. (1960) Proc. Natl. Acad. Sci. USA 77:4216–4220; Rungold et al. (1981) J. Mol. and Appl. Genet. 1:165–175.

The above-described system can be used to direct the expression of a wide variety of procaryotic, eucaryotic and viral proteins, including, for example, viral glycoproteins suitable for use as vaccine antigens, immunomodulators for regulation of the immune response, hormones, cytokines and growth factors, as well as proteins useful in the production of other biopharmaceuticals.

It may also be desirable to produce mutants or analogs of the proteins of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

For purposes of the present invention, it is particularly desirable to further engineer the coding sequence to effect secretion of the polypeptide from the host organism. This enhances clone stability and prevents the toxic build up of proteins in the host cell so that expression can proceed more efficiently. Homologous signal sequences can be used for this purpose with proteins normally found in association with a signal sequence. Additionally, heterologous leader sequences which provide for secretion of the protein can be added to the constructs. Preferably, processing sites will be included such that the leader fragment can be cleaved from the protein expressed therewith. (See, e.g., U.S. Pat. No. 4,336,246 for a discussion of how such cleavage sites can be introduced). The leader sequence fragment typically encodes a signal peptide comprised of hydrophobic amino acids.

In one embodiment of the invention, a heterologous gene sequence, i.e., a therapeutic gene, is inserted into the nucleic acid molecule of the invention. Other embodiments of the isolated nucleic acid molecule of the invention include the addition of a single enhancer element or multiple enhancer elements which amplify the expression of the heterologous therapeutic gene without compromising tissue specificity.

The transformation procedure used depends upon the host to be transformed. Mammalian cells can conveniently be transformed using, for example, DEAE-dextran based procedures, calcium phosphate precipitation (Graham, F. L. and Van der Eb, A. J. (1973) Virology 52:456–467), protoplast fusion, liposome-mediated transfer, polybrene-mediated transfection and direct microinjection of the DNA into nuclei. Bacterial cells will generally be transformed using calcium chloride, either alone or in combination with other divalent cations and DMSO (Sambrook, Fritsch & Maniatis, Molecular Cloning: A Laboratory Manual, Second Edition (1989)). DNA can also be introduced into bacterial cells by electroporation. Methods of introducing exogenous DNA into yeast hosts typically include either the transformation of spheroplasts or transformation of intact yeast cells treated with alkali cations.

The constructs can also be used in gene therapy or nucleic acid immunization, to direct the production of the desired gene product in vivo, by administering the expression constructs directly to a subject for the in vivo translation thereof. See, e.g. EPA Publication No. 336,523 (Dreano et al., published Oct. 11, 1989). Alternatively, gene transfer can be accomplished by transfecting the subject's cells or tissues with the expression constructs ex vivo and reintroducing the transformed material into the host. The constructs can be directly introduced into the host organism, i.e., by injection (see International Publication No. WO/90/11092; and Wolff et al., (1990) Science 247:1465–1468). Liposome-mediated gene transfer can also be accomplished using known methods. See, e.g., Hazinski et al., (1991) Am. J. Respir. Cell Mol. Biol. 4:206–209; Brigham et al. (1989) Am. J. Med. Sci. 298:278–281; Canonico et al. (1991) Clin. Res. 39:219A; and Nabel et al. (1990) Science 249:1285–1288. Targeting agents, such as antibodies directed against surface antigens expressed on specific cell types, can be covalently conjugated to the liposomal surface so that the nucleic acid can be delivered to specific tissues and cells for local administration.

Human Gene Therapy and Diagnostic Use of Vector

There are several protocols for human gene therapy which have been approved for use by the Recombinant DNA Advisory Committee (RAC) which conform to a general protocol of target cell infection and administration of transfected cells (see for example, Blaese, R. M., et al., 1990; Anderson, W. F., 1992; Culver, K. W. et al., 1991). In addition, U.S. Pat. No. 5,399,346 (Anderson, W. F. et al., Mar. 21, 1995, U.S. Ser. No. 220,175) describes procedures for retroviral gene transfer. The contents of these support references are incorporated in their entirety into the subject application. Retroviral-mediated gene transfer requires target cells which are undergoing cell division in order to achieve stable integration hence, cells are collected from a subject often by removing blood or bone marrow. It may be necessary to select for a particular subpopulation of the originally harvested cells for use in the infection protocol. Then, a retroviral vector containing the gene(s) of interest would be mixed into the culture medium. The vector binds to the surface of the subject's cells, enters the cells and inserts the gene of interest randomly into a chromosome. The gene of interest is now stably integrated and will remain in place and be passed to all of the daughter cells as the cells grow in number. The cells may be expanded in culture for a total of 9–10 days before reinfusion (Culver et al., 1991). As the length of time the target cells are left in culture increases, the possibility of contamination also increases, therefore a shorter protocol would be more beneficial.

This invention provides for the construction of retrovirus vectors containing the PEG-3 promoter or a functional equivalent thereof linked to a gene of interest for use in gene therapy or for diagnostic uses. The efficiency of transduction of these vectors can be tested in cell culture systems.

Uses of the Compositions of the Invention

This invention involves targeting a gene-of-interest to the a cancer cell so that the protein encoded by the gene is expressed and directly or indirectly ameliorate the diseased state. Since the PEG-3 promoter is specifically active in a cancer cell which is undergoing cancer progression, it will act as a tissue specific promoter (specific for cancer cells).

After infecting a susceptible cell, the transgene driven by a specific promoter in the vector expresses the protein encoded by the gene. The use of the highly specific gene vector will allow selective expression of the specific genes in cancer cells.

The basic tasks in the present method of the invention are isolating the gene of interest, selecting the proper vector vehicle to deliver the gene of interest to the body, administering the vector having the gene of interest into the body, and achieving appropriate expression of the gene of interest. The present invention provides packaging the cloned genes, i.e. the genes of interest, in such a way that they can be injected directly into the bloodstream or relevant organs of patients who need them. The packaging will protect the foreign DNA from elimination by the immune system and direct it to appropriate tissues or cells.

In one embodiment of the invention, the gene of interest (desired coding sequence) is a tumor suppressor gene. The tumor suppressor gene may be p21, RB (retinoblastoma) or p53. One of skill in the art would know of other tumor suppressor genes. Recent U.S. Pat. Nos. 6,025,127 and 5,912,236 are hereby incorporated by reference to more explicitly describe the state of the art as to tumor suppressor genes.

Along with the human or animal gene of interest another gene, e.g., a selectable marker, can be inserted that will allow easy identification of cells that have incorporated the modified retrovirus. The critical focus on the process of gene therapy is that the new gene must be expressed in target cells at an appropriate level with a satisfactory duration of expression.

The methods described below to modify vectors and administering such modified vectors into the skin are merely for purposes of illustration and are typical of those that might be used. However, other procedures may also be employed, as is understood in the art.

Most of the techniques used to construct vectors and the like are widely practiced in the art, and most practitioners are familiar with the standard resource materials which describe specific conditions and procedures. However, for convenience, the following paragraphs may serve as a guideline.

General Methods for Vector Construction

Construction of suitable vectors containing the desired therapeutic gene coding and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of these commercially available restriction enzymes (See, e.g. New England Biolabs Product Catalog). In general, about 1 µg of plasmid or DNA sequences is cleaved by one unit of enzyme in about 20 µl of buffer solution. Typically, an excess of restriction enzyme is used to insure complete digestion of the DNA substrate.

Incubation times of about one hour to two hours at about 37 degree. C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods in Enzymology 65:499–560 (1980). Restriction cleaved fragments may be blunt ended by treating with the large fragment of E. coli DNA polymerase I (Klenow) in the presence of the four deoxynucleotide triphosphates (dNTPs) using incubation times of about 15 to 25 min at 20 degree. C. to 25 degree. C. in 50 mM Tris (pH 7.6) 50 mM NaCl, 6 mM $MgCl_2$, 6 mM DTT and 5–10 .mu.M dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 10–50 µl volumes under the following standard conditions and temperatures using T4 DNA ligase. Ligation protocols are standard (D. Goeddel (ed.) Gene Expression Technology: Methods in Enzymology (1991)). In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Alternatively, religation can be prevented in vectors which have been double digested by additional restriction enzyme digestion of the unwanted fragments.

Suitable vectors include viral vector systems e.g. ADV, RV, and AAV (R. J. Kaufman "Vectors used for expression in mammalian cells" in Gene Expression Technology, edited by D. V. Goeddel (1991).

Many methods for inserting functional DNA transgenes into cells are known in the art. For example, non-vector methods include nonviral physical transfection of DNA into cells; for example, microinjection (DePamphilis et al., Bio-Technique 6:662–680 (1988)); liposomal mediated transfection (Felgner et al., Proc. Natl. Acad. Sci. USA, 84:7413–7417 (1987), Felgner and Holm, Focus 11:21–25 (1989) and Felgner et al., Proc. West. Pharmacol. Soc. 32: 115–121 (1989)) and other methods known in the art.

Administration of Modified Vectors Into Subject

One way to get DNA into a target cell is to put it inside a membrane bound sac or vesicle such as a spheroplast or liposome, or by calcium phosphate precipitation ($CaPO_4$) (Graham F. and Van der Eb, A., Virology 52:456 1973; Schaefer-Ridder M., et al., Liposomes as gene carriers: Efficient transduction of mouse L cells by thymidine kinase gene. Science 1982; 215:166; Stavridis J. C., et al., Construction of transferrin-coated liposomes for in vivo transport of exogenous DNA to bone marrow erythroblasts in rabbits. Exp Cell Res 1986; 164:568–572).

A vesicle can be constructed in such a way that its membrane will fuse with the outer membrane of a target cell. The vector of the invention in vesicles can home into the cancer cells.

The spheroplasts are maintained in high ionic strength buffer until they can be fused through the mammalian target cell using fusogens such as polyethylene glycol.

Liposomes are artificial phospholipid vesicles. Vesicles range in size from 0.2 to 4.0 micrometers and can entrap 10% to 40% of an aqueous buffer containing macromolecules. The liposomes protect the DNA from nucleases and facilitate its introduction into target cells. Transfection can also occur through electroporation. Before administration, the modified vectors are suspended in complete PBS at a selected density for injection. In addition to PBS, any osmotically balanced solution which is physiologically compatible with the subject may be used to suspend and inject the modified vectors into the host.

For injection, the cell suspension is drawn up into the syringe and administered to anesthetized recipients. Multiple injections may be made using this procedure. The viral suspension procedure thus permits administration of genetically modified vectors to any predetermined site in the skin, is relatively non-traumatic, allows multiple administrations simultaneously in several different sites or the same site using the same viral suspension. Multiple injections may consist of a mixture of therapeutic genes.

Survival of the Modified Vectors so Administered

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Banerji et al., Cell 27:299 (1981); Corden et al., Science 209:1406 (1980); and Breathnach and Chambon, Ann. Rev. Biochem. 50:349 (1981)). For retroviruses, control elements involved in the replication of the retroviral genome reside in the long terminal repeat (LTR) (Weiss et al., eds., In: The molecular biology of tumor viruses: RNA tumor viruses, Cold Spring Harbor Laboratory, Cold Spring Harbor, N.Y. (1982)).

Moloney murine leukemia virus (MLV) and Rous sarcoma virus (RSV) LTRs contain promoter and enhancer sequences (Jolly et al., Nucleic Acids Res. 11:1855 (1983); Capecchi et al., In: Enhancer and eukaryotic gene expression, Gulzman and Shenk, eds., pp. 101–102, Cold Spring Harbor Laboratories, Cold Spring Harbor, N.Y.).

Promoter and enhancer regions of a number of non-viral promoters have also been described (Schmidt et al., Nature 314:285 (1985); Rossi and de Crombrugghe, Proc. Natl. Acad. Sci. USA 84:5590–5594 (1987)).

In addition to using viral and non-viral promoters to drive therapeutic gene expression, an enhancer sequence may be used to increase the level of therapeutic gene expression. Enhancers can increase the transcriptional activity not only of their native gene but also of some foreign genes (Armelor, Proc. Natl. Acad. Sci. USA 70:2702 (1973)).

Therapeutic gene expression may also be increased for long term stable expression after injection using cytokines to modulate promoter activity.

The methods of the invention are exemplified by preferred embodiments in which modified vectors carrying a therapeutic gene are injected intracerebrally into a subject.

The most effective mode of administration and dosage regimen for the molecules of the present invention depends upon the exact location of the cancer being treated, the severity and course of the cancer, the subject's health and response to treatment and the judgment of the treating physician. Accordingly, the dosages of the molecules should be titrated to the individual subject. The molecules may be delivered directly or indirectly via another cell, autologous cells are preferred, but heterologous cells are encompassed within the scope of the invention.

The interrelationship of dosages for animals of various sizes and species and humans based on mg/m.sup.2 of surface area is described by Freireich, E. J., et al. Cancer Chemother., Rep. 50 (4):219–244 (1966). Adjustments in the dosage regimen may be made to optimize the tumor cell growth inhibiting and killing response, e.g., doses may be divided and administered on a daily basis or the dose reduced proportionally depending upon the situation (e.g., several divided dose may be administered daily or proportionally reduced depending on the specific therapeutic situation).

It would be clear that the dose of the molecules of the invention required to achieve cures may be further reduced with schedule optimization.

Use of PEG-promoter to Direct High Expression of a Heterlogus Gene in Cancer Cells One embodiment of the invention provides for methods for expressing a gene of interest which gene is not endogenously expressed in cancer cells which comprises a) constructing a nucleic acid which comprises the PEG-3 promoter operatively linked to the gene-of-interest; b) introducing this nucleic acid into a cancer cell which cell expresses PEG-3, thereby causing the PEG-3 promoter to direct expression of the gene-of-interest in the cancer cell. In one embodiment, the gene-of-interest encodes a protein which is cytotoxic to the cancer cell, causes apoptosis of the cancer cell, slows the growth of the cancer cell, or causes the cancer cell to stop dividing. The gene-of-interest can be any gene whose expression would cause a desired biochemical or physiological effect in the cancer cell, such as the decrease of growth or the decrease or inhibition of cancer phenotype progression.

One advantage of using the nucleic acid construct described above in such a method to treat cancer in a subject, is that the nucleic acid can be administered to both cancerous and normal cells. However, since the PEG-3 promoter is only active in cancerous cells, there will be no expression of the gene-of-interest in normal cells, while there will be high expression of the gene-of-interest in the cancerous cells. This nucleic acid construct thus allows one to target specifically expression of a gene-of-interest to specifically cancerous cells.

Liposomes could be used as a delivery agent to introduce the nucleic acid construct to the cells of the subject to be treated. Of course, there are many ways to deliver such a nucleic acid construct which would be known to one of skill in the art (e.g. microinjection; topical application; use of a chemical vehicle; direct injection into the tumor; etc.).

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1: Defining the Regions Within the Promoter of Progression Elevated Gene-3 Responsible for Differential Expression During Transformation Progression Cancer is a progressive disease in which a tumor cell temporally develops qualitatively new transformation related phenotypes or a further elaboration of existing transformation associated properties. A rodent cell culture model system is being used to define the genes that associate with and control cancer progression. Subtraction hybridization identified a novel gene that is functionally involved in the induction of transformation progression in mutant adenovirus type 5, H5ts125, transformed rat embryo cells, referred to as progression elevated gene-3 (PEG-3). A 5'-flanking promoter region of ~2.1 kilobases, PEG-promoter, has been isolated, cloned and characterized. The full-length and various mutated regions of the PEG-promoter have been linked to a luciferase reporter construct and evaluated for promoter activity during cancer progression using transient transfection assays. These experiments demonstrate a requirement for AP-1 and PEA-3 sites adjacent to the TATA box region of PEG-3 in mediating enhanced expression of PEG-3 in progressed versus un-progressed H5-ts125-transformed rat embryo cells. An involvement of AP-1 and PEA-3 in PEG-3 regulation was also demonstrated by protein blotting, electrophoretic mobility shift (EMSA) assays and transfection studies with PEA-3 and c-Jun expression vectors. Our findings document the importance of the AP-1 and PEA-3 transcription factors in mediating elevated expression of PEG-3 in H5ts125-transformed rat embryo cells displaying an aggressive and progressed cancer phenotype.

Example 2: Cooperation Between AP-1 and PEA-3 Sites Within the Progression Elevated Gene-3 (PEG-3) Promoter Regulate Basal and Differential Expression of PEG-3 During Progression of the Oncogenic Phenotype in Transformed Rat Embryo Cells The carcinogenic process involves a series of sequential changes in the phenotype of a cell, resulting in new properties or a further elaboration of transformation-associated traits by the evolving tumor cell (Fisher, 1984; Bishop, 1991; Knudson, 1993; Vogelstein and Kinzler, 1993). Although extensively studied, the precise genetic mechanisms underlying tumor cell progression during the development of most human cancers remain unknown. Experimental evidence indicates that a number of diverse acting genetic elements can contribute to cancer development and transformation progression (Fisher, 1984; Bishop, 1991; Liotta et al., 1991; Knudson, 1993; Levine, 1993; Hartwell and Kastan, 1994; Kang et al., 1998a; Vogelstein and Kinzler, 1993; Su et al., 1997; 1999). Important target genes involved in these processes include, oncogenes, tumor supressor genes and genes regulating genomic stability, cancer agressiveness and angiogenesis (Fisher, 1984; Bishop, 1991; Liotta et al., 1991; Knudson, 1993; Levine, 1993; Hartwell and Kastan, 1994; Kang et al., 1998a; Vogelstein and Kinzler, 1993; Su et al., 1997, 1999). Recently, several novel genetic elements have been identified that associate with or in specific instances directly regulate cancer agressiveness, i.e. progression elevated (PEGen) and progression suppressed (PSGen) genes (Kang, et al., 1998a; Su et al., 1997, 1999). The precise mechanism by which these different genes orchestrate the complex process of cancer progression represent an important area of investigation with potential for defining novel pathways and target molecules that could lead to new diagnostic and therapeutic approaches for cancer.

A useful model for defining the genetic and biochemical changes mediating tumor progression is the Ad5/early passage RE cell culture system (Fisher, 1984; Babiss et al., 1985; Duigou et al., 1989, 1990, 1991; Fisher et al, 1979a, b,c; Reddy et al., 1993; Su et al., 1994, 1997; Kang et al., 1998a). Transformation of secondary rat embryo (RE) cells by Ad5 is often a sequential process resulting in the acquisition of an further elaboration of specific phenotypes by the untransformed cell (Fisher et al., 1979 a,b,c; Babiss et al, 1985). Progression in the Ad5-transformation model is characterized by the development of enhanced anchorage-independence and tumorigenic capacity (as formation in nude mice) (Fisher, 1984; Babiss et al., 1985). The progression phenotype in Ad5-transformed RE cells can be induced by selection for growth in agar or tumor formation in nude mice (Fisher et al., 1979 a,b,c; Babiss et al., 1985) by transfection with oncogenes,such as Ha-ras, v-src, v-raf or the E6/E7 region of human papilloma virus type 18 (Duigou et al., 1989; Reddy et al., 1993) or by transfection with specific signal transducing genes, such as protein kinase C (Su et al., 1994).

Progression induced spontaneously or after gene transfer, is a stable cellular trait that remains undiminished in Ad5-transformed RE cells even after extensive passage (>100) in monolayer culture (Fisher, 1984; Babiss et al., 1985; Reddy et al., 1993). However, a single-treatment with the demethylating agent 5-azacytidine (AZA) results in a stable reversion in transformation progression in >95% of cellular clones (Fisher, 1984; Babiss et al., 1985; Duigou et al., 1989; Reddy et al., 1993; Su et al., 1994). The progression phenotype is also suppressed in somatic cell hybrids formed between normal or un-progressed transformed cells and progressed cells (Duigou et al., 1990, 1991; Reddy et al., 1993). These findings suggest that progression may result from the activation of specific progression-promoting (progression elevated) genes or the selective inhibition of progression-suppression (progression suppressed) genes, or possibly a combination of both processes (Fisher, 1984; Babiss et al., 1985; Su et al., 1997; Kang et al., 1998a). To identify potential progression inducing genes with elevated expression in progressed versus un-progressed Ad5 transformed cells, we are using subtraction hybridization and reciprocal subtraction differential RNA display (RSDD) approaches (Jiang and Fisher, 1993; Reddy et al., 1993; Su et al., 1997; Kang et al., 1998a). The subtraction hybridization approach resulted in cloning of PEG-3 which displays elevated expression in progressed cells (spontaneous, oncogene-induced or growth-factor related gene-induced) than in un-progressed cells (parental Ad5-transformed, AZA-suppressed, and suppressed somatic cell hybrids) (Su et al, 1997). These findings document a direct correlation between expression of PEG-3 and the progression phenotype in this rat embryo model system.

Nuclear run-on assays confirm a direct correlation between PEG-3 expression and an increase in the rate of RNA transcription of this gene (Su et al., 1997). To elucidate the mechanism underlying the differential expression of PEG-3 during transformation progression the 5'-flanking region of this gene which contains the promoter (PEG-Prom) has been isolated and characterized. The full-length ~2.0 kb PEG-Prom and various mutations (including deletions and point mutations) in PEGProm were constructed and analysed. The results of this inquiry demonstrate that AP1 and PEA3 transcription factors are the primary determinants of the elevated expression of PEG-3 in progressed Ad5-transformed RE cells. This conclusion is verified by electrophoretic mobility shift assays (EMSA) and transfection studies with c-Jun and PEA3 expression vectors.

Results
Expression of PEG3 Directly Correlates With Transformation Progression

Figure 1B:
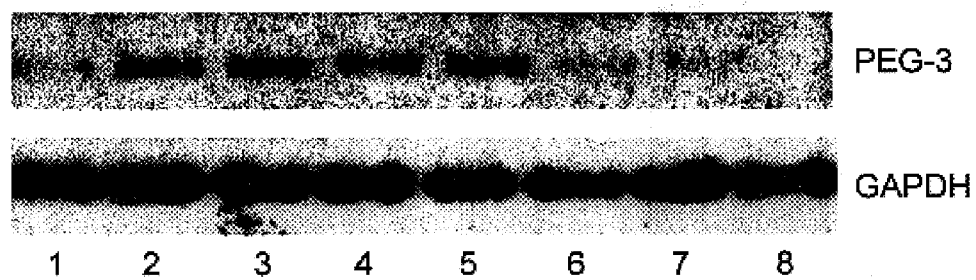

To evaluate the relationship between PEG-3 expression and transformation progression we have used a series of rodent cell lines that span the gamut from normal to highly progressed (Fisher et al. 1987; Babiss et al., 1985; Duigou et al., 1989; Reddy, et al., 1993; Su et al., 1997, 1999). A hallmark of the progression phenotype in this rodent model is the ability to grow with enhanced efficiency in an anchorage-independent manner and to induce tumors in nude mice with a reduced tumor latency time (18–21 days as opposed to 38–44 days, respectively) (Babiss et al., 1985; Su et al, 1999). A specific H5ts125-transformed secondary Sprague-Dawley RE clone, E11, grows in agar with low efficiency (~2–4%) (progression negative), whereas a highly progressed nude mouse tumor-derived E11 subclone, E11-NMT, grows with high efficiency in agar (~30–45%) (FIG. 1A). Forced expression of the Ha-ras oncogene in E11 cells, E11-ras R12 as a representative clone, results in acquisition of the progression phenotype as indicated by both anchorage-independent growth (FIG. 1A) and tumor latency time in nude mice (Reddy et al., 1993). Quantifying PEG-3 mRNA levels by Northern hybridization (FIG. 1B) and PEG-3 protein levels by Western blotting (FIG. 1C) indicates a direct correlation between PEG-3 expression, elevated in E11-NMT and E11-ras R12 and reduced in E11, and expression of the progression phenotype (as indicated by anchorage independent growth).

Figure 1C:
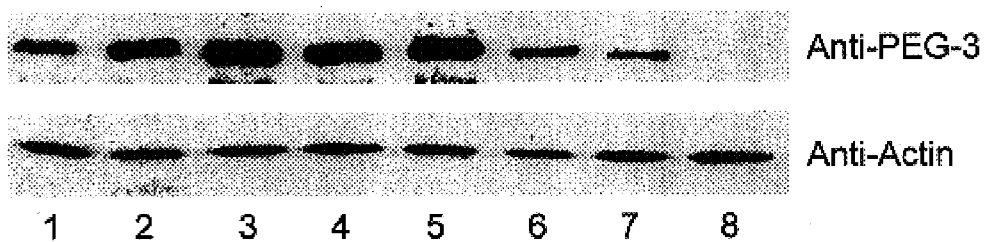

To explore further the relationship between PEG-3 expression and progression, the same three parameters as measured for E11, E11-NMT and E11-ras R12 cells were used to compare a series of somatic cell hybrids formed between E11-NMT and CREF cells (FIG. 1). CREF cells are immortal rat embryo cells that do not form colonies when grown in agar and are devoid of tumorigenic potential when inoculated subcutaneously into athymic nude mice (Fisher et al., 1982; Duigou et al., 1990). Similarly, somatic cell hybrids formed between E11-NMT and CREF cells that display a fat morphology such as F1 and F2, also fail to form tumors in nude mice (Duigou et al., 1990), although they grow with a low efficiency in agar similar to E11 cells (FIG. 1A). In contrast, specific E11-NMT×CREF somatic cell hybrids that display round morphology such as R1 and R2, grown with high efficiency in agar, even exceeding that of E11-NMT (FIG. 1A) and they rapidly form tumors in nude mice (Duigou et al., 1990). As observed with E11 cells, the levels of PEG-3 mRNA and protein are reduced in F1 and F2 cells, whereas R1 and R2 display elevated expression of PEG-3 akin to that of E11-NMT and E11-ras R12 cells (FIGS. 1B, 1C). In the case of CREF cells, PEG-3 mRNA is detected at very low levels by Northern blotting (FIG. 1B) and PEG-3 protein is barely detectable by Western blotting (FIG. 1C). These results indicate a direct concordance between PEG-3 expression and the progression phenotype in H5ts125-transformed RE cells.

Figure 3:
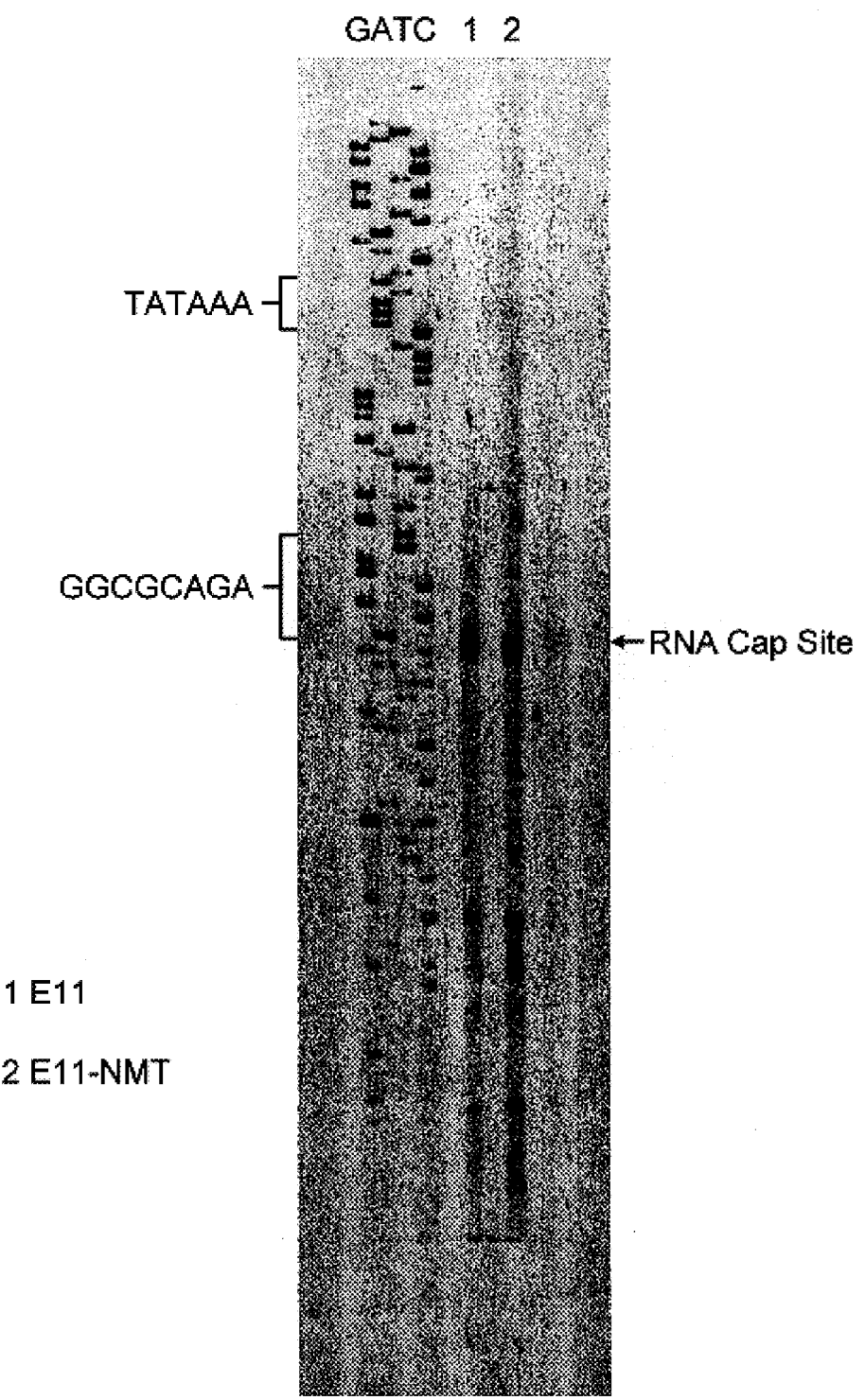
FIG. 3: Determination of the transcription start site of the PEG-3 promoter. A primer complementary to the 5' UTR region of PEG-3 mRNA (see Materials and Methods hereinbelow) was annealed with 4 µg of Poly A$^+$ RNAs from E11-NMT or E11 cells and used as a template for the primer extension assay. The conditions used for reverse transcription were as described in Materials and Methods. A DNA sequencing reaction, using the same primer and PEG-3 promoter as the template, was electrophoresed in parallel in the same gel with the primer extension reaction.

Isolation of the PEG-3 Promoter and Identification of the Transcription Start Site Based on the sequence of the PEG-3 cDNA, a genomic walking approach from the 5' region of the PEG-3 cDNA was used to identify a 2.0-kb rat genomic fragment that represents the 5' flanking region of the PEG-3 gene. The sequence of the putative FL-PEG-Prom, is shown in FIG. 2. The transcription start site of the PEG-3 gene was mapped by primer extension with RNAs isolated from E11 and E11-NMT cells (FIG. 3). Computer analysis with GCG software of the PEG-Prom indicates the presence of two TATA boxes located at positions −1071 and −24 upstream of the RNA cap site, respectively. The sequence at −1071 is probably non-functional because of its large distance from the RNA cap-site. Two PEA3-binding sites, AGGAAA and TTTCCT, are located at positions −1644 and −101. The PEA3 site at position −101 is 76 nt upstream of the TATA box. An AP1 site is present at position +8. Additional potential DNA binding elements are also apparent in the PEG-Prom, including SpI, acute phase reaction element, NFKB1, E2F, E2A, GRE, TRE and CREB.

Figure 4:
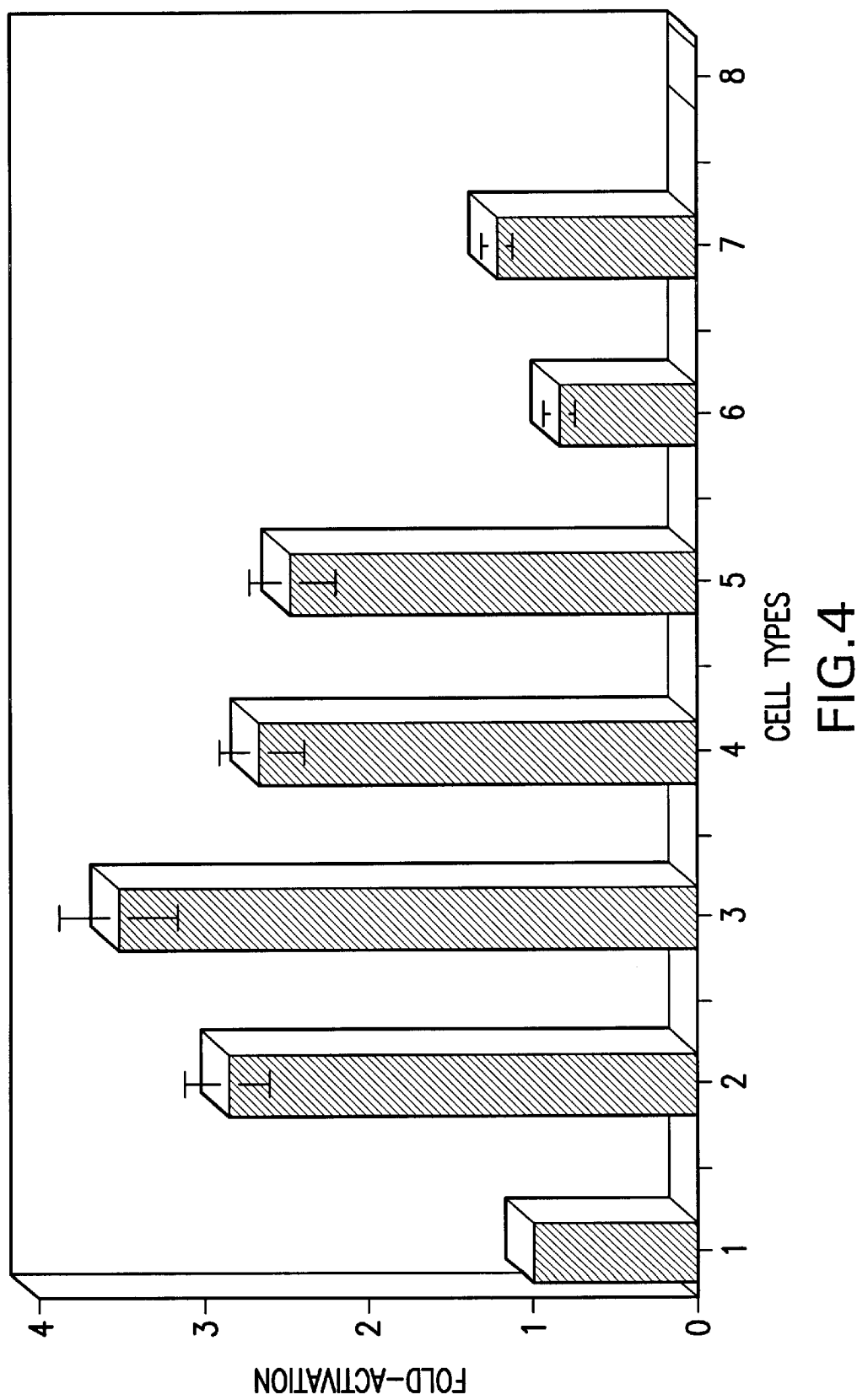
FIG. 4: Full-length PEG-3 promoter-luciferase activity in normal, adenovirus transformed and somatic cell hybrid rodent cells. Different cell types were co-transfected with 5 µg of the FL PEG-Prom and 1 µg of a pSV-β-galactosidase plasmid and luciferase activity was determined as described in Materials and Methods 48 hr later. The results are standardized by β-galactosidase activity and represent the average of 3 independent experiments±SD. Results are expressed as fold activation in comparison with activity in E11, which represents 1 fold activation.

AP1 and PEA3 sites adjacent to the TATA box in the PEG-3 promoter are involved in basal and enhanced promoter activity in progressed and un-progressed H5ts125transformed RE cells Transfection of the FL-PEG-Prom luciferase construct into the different cell types demonstrated a direct relationship between expression of the progression phenotype and elevated promoter activity (FIG. 4). Progressed cells displayed a 2.5- to 3.5-fold increase in luciferase activity, a value that compares well with PEG-3 Northern and Western blotting data (FIGS. 1B and 1C). The level of luciferase activity in E11 cells was similar to that observed in the F1 and F2 CREF×E11-NMT somatic cell hybrids. In the case of actively proliferating CREF cells, the PEG-prom exhibited negligible activity.

Figure 5A:
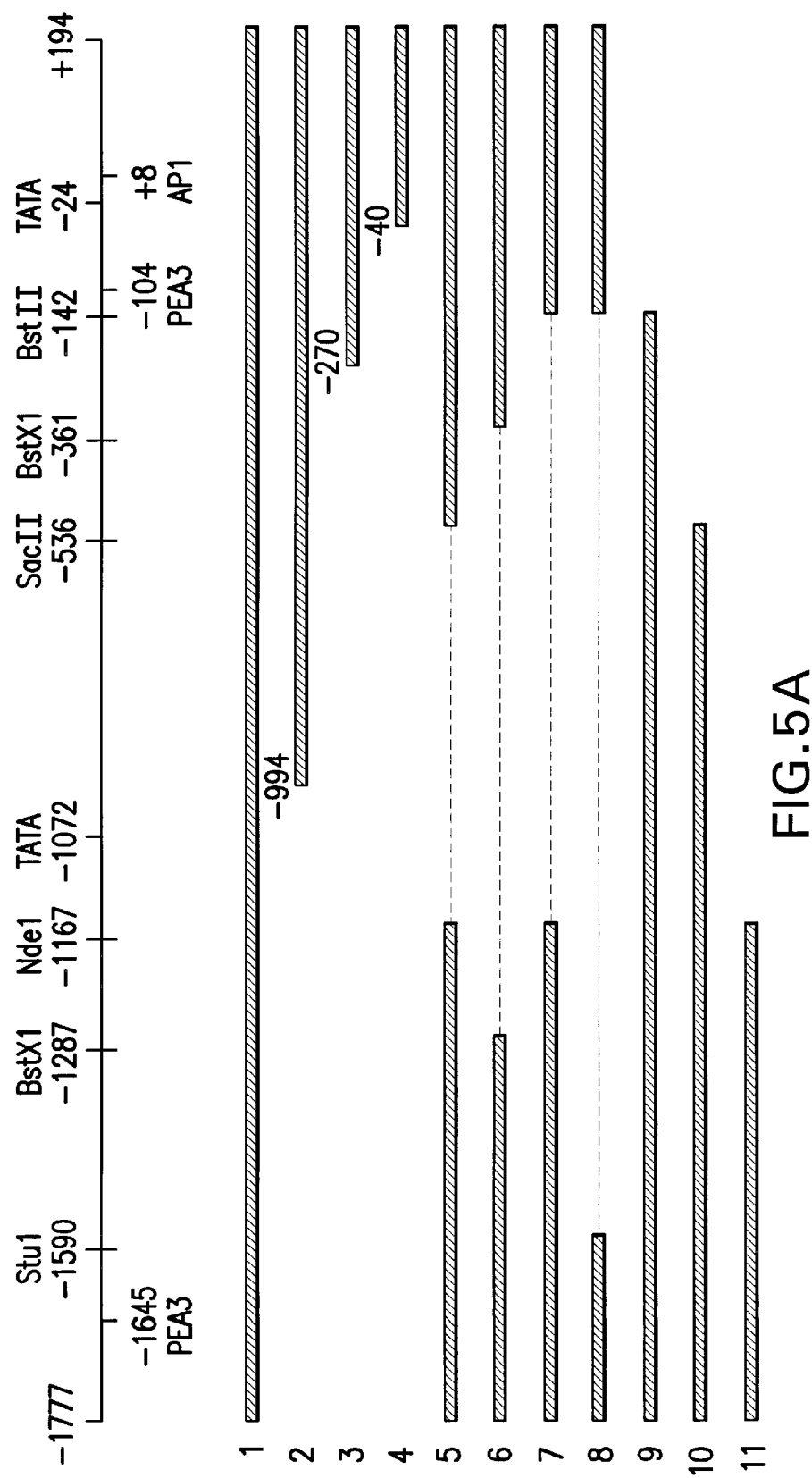
FIGS. 5A–5B: Mapping the regions of the PEG-3 promoter necessary for basal and elevated PEG-Prom expression in E11 and E11-NMT cells.
Figure 5B:
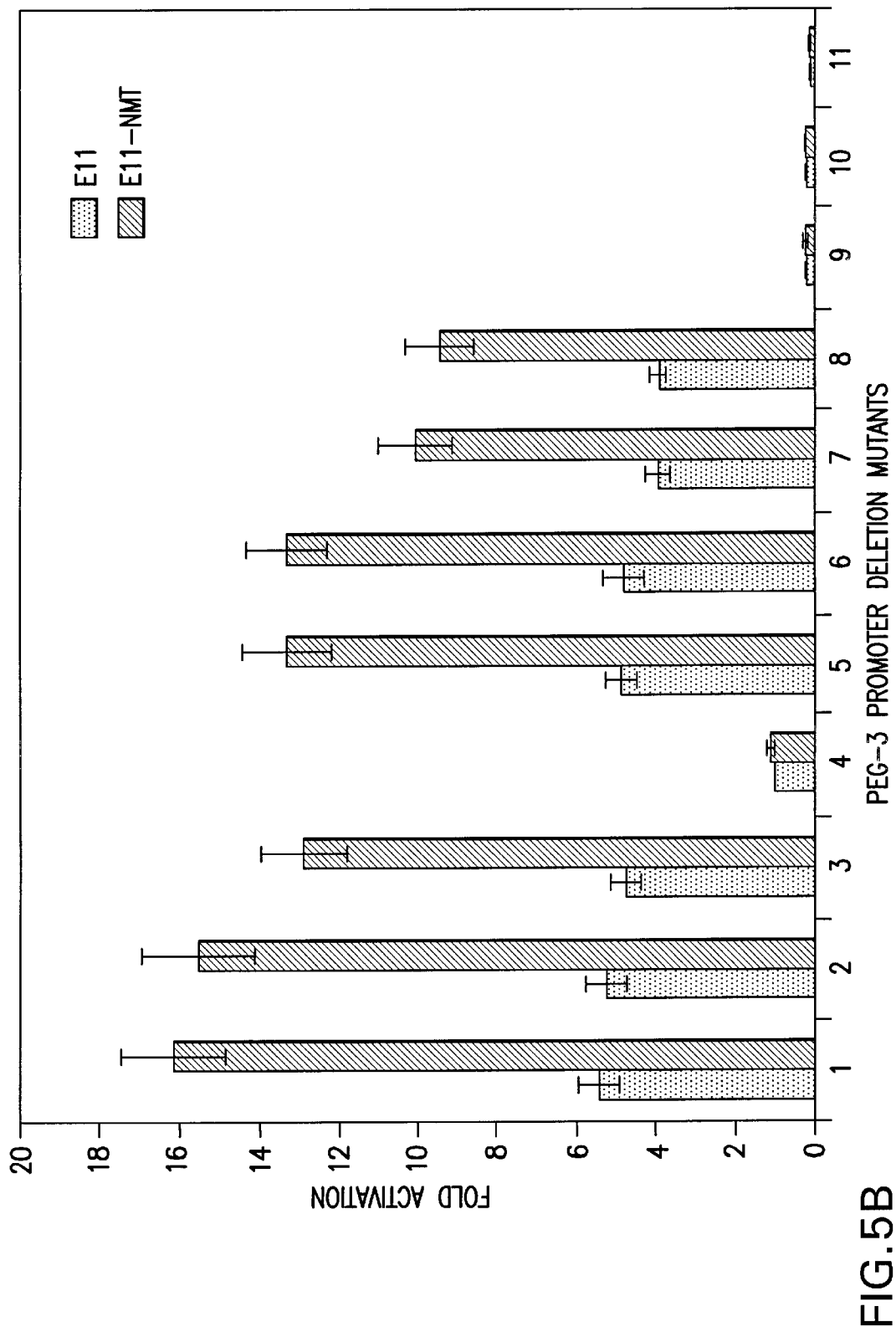
Figure 6A:
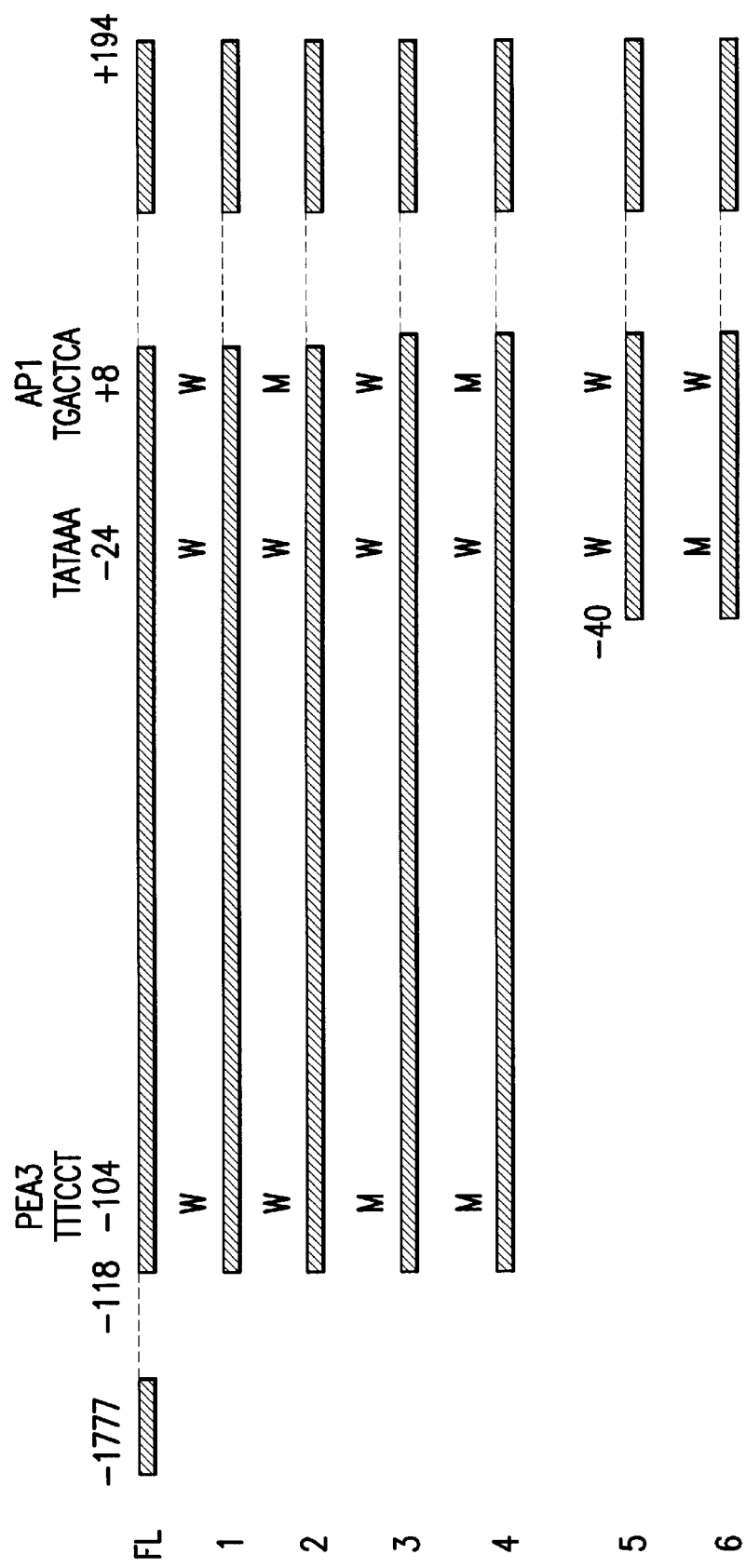
FIGS. 6A–6B: Mutation analysis of the PEA3 and AP1 sites and the TATA box in the PEG-Prom.

To define the region(s) of the FL-PEG-Prom involved in the differential expression of the PEG-3 gene during progression of the transformed phenotype in H5ts125-transformed cells, a series of PEG-Prom deletion constructs were engineered and placed in front of the luciferase gene (FIGS. 5 and 6). Deletion of the PEA3 site at position −1645 and the TATA box at position −1072 did not effect PEG promoter activity in either E11 or E11-NMT suggesting that these regions of the promoter do not contribute to basal or enhanced expression of the PEG-Prom in E11 or E11-NMT cells (FIG. 5). A further deletion at position −270 minimally inhibited promoter activity in E11-NMT cells (~19% reduction versus activity of the FL-PEG-Prom) without significantly altering activity of the PEG-Prom in E11 cells. In contrast, removal of the PEA3 site at −104 nt with retention of the TATA box at position −24 and the AP1 site at +8 bp resulted in a reduction in basal promoter activity in both E11 and E11-NMT cells. The activity of this mutant PEG-Prom was 15- and 4-fold lower, respectively, than the activity of the FL-PEG-Prom in E11-NMT and E11 cells (FIG. 5). In effect, this promoter deletion eliminated the enhanced expression of the PEG-Prom in E11-NMT versus E11 cells, indicating that the PEA3 site at −104 is a primary determinant of the enhanced activity of PEG-3 in progressed H5ts125-transformed RE cells. Internal deletions at position −1167 to −536 and −1287 to −361 resulted in similar levels of luciferase activity in E11-NMT and E11 cells as observed with the deletion mutant containing a deletion at position −270. Internal deletions engineered between −1167 to −142 and −1590 to −142 resulted in a further decrease in promoter activity in both E11 and E11-NMT cells, with the most profound effect apparent in E11-NMT cells (~41% reduction in activity in comparison with the FL-PEG-Prom). In contrast, deletion of the promoter regions from −142, −536 or −1167 with retention of the remainder of the PEG-Prom completely abolished PEG promoter activity (FIG. 5). These results implicate the PEA3 transcription site (at position −104), the AP1 transcription site (at position +8) and the TATA box (at position −24) as primary determinants of basal PEG-Prom activity in E11 and E11-NMT cells.

To examine further the role of the PEA3 site at position −104, the TATA box at position −24 and the AP1 site at position +8 in the regulation of PEG-3 promoter activity in E11 and E11-NMT cells an additional series of mutant PEG-3 promoter luciferase constructs were generated (FIG. 6). Mutation in the AP1 site, with retention of the wt PEA3 and TATA sites, resulted in equivalent promoter activity in E11 and E11-NMT cells. This observation emphasizes the importance of the AP1 site at position +8 in the PEG promoter in regulating elevated PEG-3 transcriptional activity in E11-NMT versus E11 cells. An involvement of the PEA3 site at position −104 in defining PEG promoter activity was also demonstrated by analysis of a construct containing a mutated PEA3 site at −104 with wild-type TATA (at position −24) and AP1 (at position +8) sites (FIG. 6). In this mutant, the level of activity of the promoter was at a basal level and the activity was similar in E11 and E11-NMT cells. A similar basal promoter activity was also observed with two additional mutants, one containing mutant AP1 and PEA3 sites and a wild-type TATA box and a mutant lacking the PEA3 site at position −104 with wild-type TATA and AP1 sites. In contrast, a mutant lacking the PEA3 site at position −104 with a mutated TATA site and a wild-type AP1 site at position +8 displayed no promoter activity. These results confirm that both the AP1 site located at +8 and the PEA3 site at position −104 are involved in the differential expression of the PEG-Prom in E11-NMT versus E11 cells. AP1 and PEA3 are major determinants of the differential expression of the PEG-Prom in E11-NMT versus E11 cells and basal PEG-Prom activity in E11 and E11-NMT cells.

Progressed E11-NMT Cells Display Enhanced Nuclear Transcription Factor Binding

Western blotting analysis was performed to determine the levels of AP1/cJun and PEA3 protein in E11 and E11-NMT cells. With both proteins the de novo level of expression was ~1.5 to 2fold higher in E11-NMT versus E11 cells (data not shown). EMSA were performed to determine the DNA binding potential of the AP1 and PEA3 proteins and if different levels of binding complexes are present in E11-NMT versus E11 cells (FIGS. 7A and 7B, respectively). Using a wild-type AP1 oligonucleotide, the level of binding to AP1 was higher in E11-NMT versus E11 (FIG. 7A). The specificity of this binding to AP1 was demonstrated by competition with a 10- and a 100-fold molar excess of unlabeled competitor and the absence of a DNA-protein complex when using a mutant AP1 oligonucleotide (FIG. 7A). Direct confirmation of binding of nuclear extracts to AP1 was provided by supershift assays using cJun (AP1) antibody (FIG. 7A). In contrast, no supershifted DNA-protein complexes were observed when an anti-actin antibody was used in place of the cJun (AP1) antibody. Similar results were obtained when a PEA3 oligonucleotide was used in gel retardation assays (FIG. 7B). Enhanced binding to PEA3 was observed with extracts from E11-NMT versus E11 cells. No binding was observed with a mutated PEA3 oligonucleotide, unlabelled PEA3 competitor effectively inhibited binding to PEA3 and antibodies specific for PEA3, but not anti-actin antibodies, resulted in supershifted DNA-protein complexes in the EMSA (FIG. 7B). These experiments demonstrate that E11-NMT cells contain elevated levels of AP1 and PEA3 with the capacity to bind to their respective sites in the promoter of PEG-3.

Ectopic Expression of cJun (AP1) and PEA3 in E11 Cells Independently and Cooperatively Enhance PEG-Prom Activity The studies described above suggested that AP1 and PEA3 sites in the PEG-Prom were responsible for the differential activity of this promoter in E11-NMT versus E11 cells. To directly determine if the proteins encoded by these transcription factors can alter the expression of the FL-PEG-Prom in E11 cells transient transfection and promoter-luciferase assays were performed (FIG. 8). Transfection of E11 cells with an expression vector producing cJun resulted in a dose-dependent increase in FL-PEG-Prom activity in E11 cells. The maximum effect obtained was small, equaling only an ~1.5-fold increase in cells not expressing the cJun expression plasmid. This stimulatory effect was not evident in cells transfected with a control vector (pcDNA3.1) or a vector encoding a mutant cJun protein (TAM67). Forced expression of PEA3 in E11 cells also resulted in a dose-dependent increase in FL-PEG-Prom activity, again reaching a maximum of ~-1.5-fold. No enhancement in promoter activity was observed in E11 cells transfected with the control pRC/RSV vector. When E11 cells were co-transfected with a combination of expression vectors producing cJun and PEA3, FL-PEG-Prom activity was comparable to that observed in E11-NMT cells. This effect was not apparent when the combination of control vectors were transfected into E11 cells (FIG. 8). These results provide support for the hypothesis that the differential expression of the PEG-Prom in E11-NMT versus E11 cells is a consequence of elevated expression of cJun (AP1) and PEA3 transcription factors in the progressed E11-NMT cells.

Discussion

Acquisition of enhanced expression of the transformed phenotype, i.e., transformation progression, represents a critical component in the cancer paradigm. A novel cDNA, PEG-3, that displays differential expression as a function of progression of the transformed phenotype, oncogenic transformation and DNA damage in rodent cells was identified by subtraction hybridization (Su et al., 1997). Recent studies document that PEG-3 is causally related to cancer progression, since ectopic expression of this gene in transformed rodent or human tumor cells results in an aggressive tumor phenotype when cells are injected subcutaneously into athymic nude mice (Su et al., 1999). These observations suggest that PEG-3 is an important contributor to transformation progression. To define the mechanism mediating differential expression of PEG-3 in progressed (E11-NMT) versus unprogressed (E11) Ad5-transformed rat embryo cells the promoter region of this gene was identified, isolated and examined. By using promoter analyses, EMSA and transient transfection assays we presently demonstrate that a combination of the AP1 and PEA3 transcription factor sites in the PEG-Prom adjacent to the TATA, region contribute to basal and enhanced promoter activity in H5ts125-transformed RE cells.

Figure 6B:
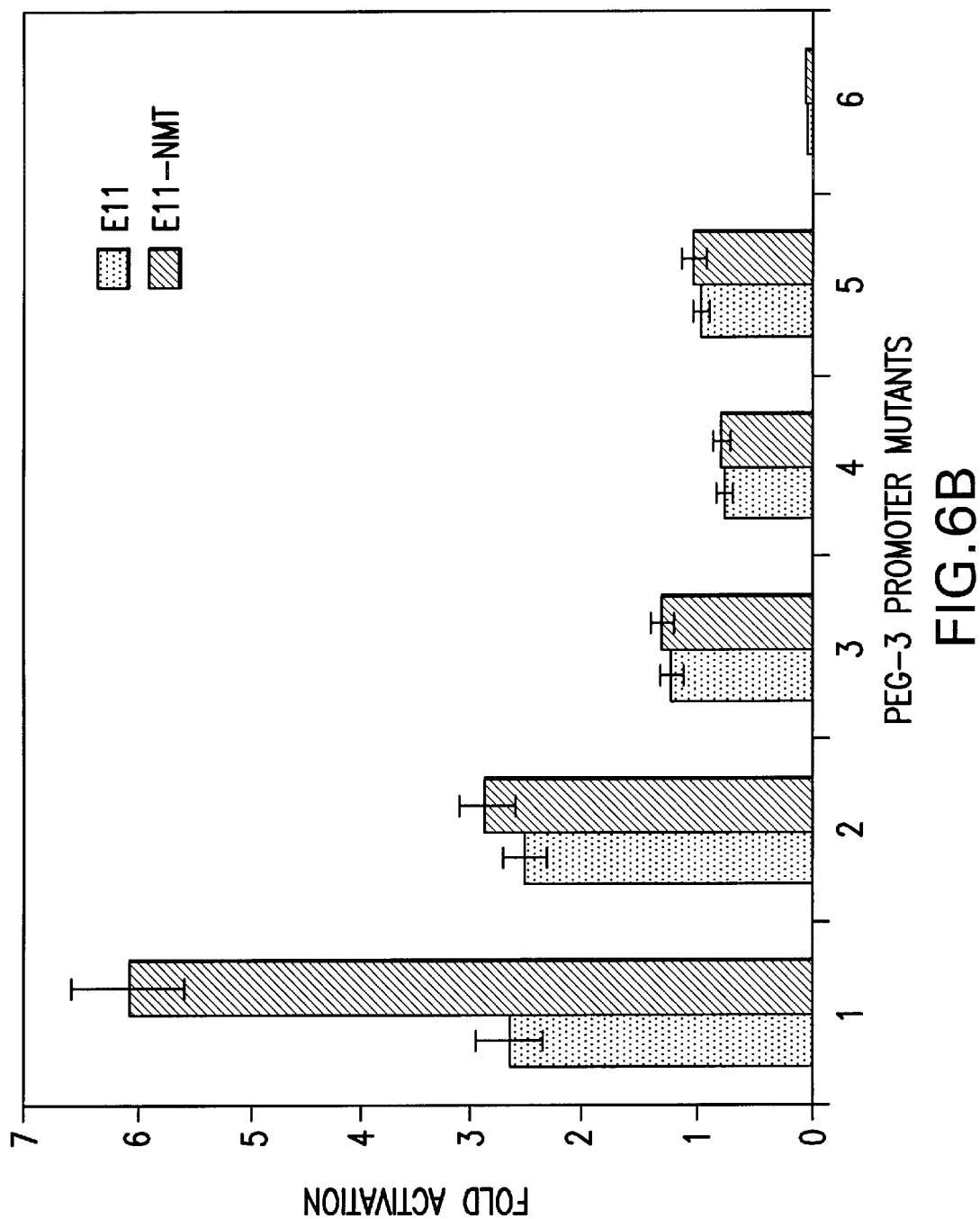

Promoter deletion analysis indicates that a region of the PEG-Prom containing −270/+194 of the PEG-3 gene is essential for PEG-3 transcriptional activity in E11 and E11-NMT cells (FIGS. 5 and 6). Moreover, this region of the PEG-Prom is also responsible for the differential promoter activity of the PEG-Prom in E11-NMT versus E11 cells. Sequence analysis indicates that this part of the PEG-Prom contains AP1 (+8), TATA (−24) and PEA3 (−104) elements (FIG. 2). A mutation of the AP1 site at +8, while retaining a wild-type TATA and PEA3 sequence, reduces the activity of the PEG-Prom deletion construct (−270/+194) in E11-NMT to that of E11 cells (FIG. 6B). This finding suggests that the AP1 site at +8 is a primary determinant of the differential expression of the PEG-Prom E11-NMT versus E11 cells. The importance of the TATA and PEA3 sites in PEG-Prom activity is also documented using additional mutants (FIG. 6B). A mutation in the PEA3 site (−104) in the presence of wild type TATA (−24) and AP1 (+8) sites reduces promoter activity in E11 and E11-NMT and effectively eliminates the enhanced activity of the PEG-Prom in E11-NMT cells. Similar levels of reduced PEG-Prom activity are apparent in both E11 and E11-NMT cells when the AP1 (+8) site is mutated singly or in combination with a mutated PEA3 (+8) site. In these contexts, altering the AP1(+8) and PEA3 (104) sites, singly or in combination, effects both basal and enhanced PEG-Prom activity. Moreover, a mutation in the TATA region (−24), even in the presence of a wild-type AP1 (+8) site, results in an extinction of promoter activity. These results demonstrate that both AP1 and PEA3 sites adjacent to an intact TATA region within the PEG-Prom contribute to both basal promoter activity in E11 and E11-NMT cells and elevated promoter activity in E11-NMT cells.

A functional interaction between the AP1 and PEA3 sites and binding of nuclear proteins in the FL-PEG-Prom was confirmed by EMSA using appropriate oligonucleotide probes and monoclonal antibodies (FIG. 7). EMSA using nuclear extracts from E11 and E11-NMT cells resulted in slower-migrating DNA-protein complexes when incubated with AP1 or PEA3 oligonucleotides (FIGS. 7A and 7B). The amount of these complexes were reduced or eliminated when a 10- or 100-fold molar excess, respectively, of unlabelled oligonucleotides were incorporated in the assay. No DNA-protein complexes were observed when a mutated AP1 or PEA3 oligonucleotide was used in the binding assay. The specificity of the nuclear protein binding was demonstrated using antibody specific for cJun (AP1) or PEA3 in the EMSA. In these experiments supershifted slow-migrating DNA-protein complexes were apparent resulting from antibody interactions with the DNA-protein complexes. The amount of AP1 and PEA3 complexes present in E11-NMT cells exceed that found in E11 cells (FIGS. 7A and 7B). Moreover, a small but significant increase (~1.5 to 2-fold) in the levels of AP1/cJun and PEA3 protein was also detected by Western blotting in E11-NMT versus E11 cells (unpublished data). The functional significance of the elevated AP1 and PEA3 proteins in E11-NMT versus E11 cells in regulating elevated PEG-3 promoter activity in the progressed cells was documented by transient transfection of cJun and PEA3 expression vectors (FIG. 8). These experiments demonstrated that transient ectopic cJun (AP1) and PEA3 expression can individually elevate PEG-Prom activity in E11 cells and the combination of both transcription factors results in an additive effect culminating in a similar PEG-Prom activity as observed in E11-NMT cells (FIG. 8). Based on increased binding activity in EMSA, increased levels of protein in Western blots and cotransfection assays there appears to be a strong correlation between PEG-3 expression and AP1/PEA3 activity.

AP1 transcription factors are immediate early response genes that regulate expression of a subset of target gene promoters containing defined sequence motifs (TPA-response elements, TRE) (Angel and Karin, 1991). The AP1 complex comprises a heterodimer of a member of the Fos family and a member of the Jun family or homodimers of members of the Jun family (Angel and Karin, 1991, Karin et al., 1997). AP1 contributes to many important and diverse biological processes including cell proliferation, transformation, onocogenesis, differentiation and apoptosis (Angel and Karin, 1991; Karin et al., 1997; Olive et al., 1997; Kang et al., 1998b). The transcription factor PEA3 a member of the ets gene family is also a major contributor to cell transformation and oncogenesis (Brown and McKnight, 1992). PEA3 proteins interact with an ~10 base pair DNA sequence in the promoters of target genes resulting in regulation of transcription (Macleod et al., 1992; Seth et al., 1992; Wasylyk et al., 1993). Putative candidate PEA3 target genes include proteinases required for degradation of the extracellular matrix, including the serine urokinase-type plasminogen activator (Nerlov et al., 1992) and matrix metalloproteinases gelatinase B, interstitial collagenase, stromelysin-3 and matrilysin (Matrisian and Bowden, 1990; Matrisian, 1994; Higashino et al., 1995), which represent important factors contributing to cancer metastasis (Liotta et al., 1991; Kohn and Liotta, 1995). Many of these extracellular matrix degrading genes also contain AP1 sites in their promoters (Angel and Karin, 1991; Karin et al., 1997). Cooperation between AP1 and PEA3 sites in regulating several cellular promoters have been documented. These include, serum growth factor response of the tissue inhibitor of metalloproteinases-1 (TIMP-1) gene (Edwards et al., 1992) and 12-0-tetradecanoylphorbol 13-acetate (TPA), fibroblast growth factor-2 (FGF-2) and macrophage colony-stimulating factor induction of the urokinase-type plasminogen activator gene (Neriov et al., 1992; Stacey et al., 1995; De Cesare et al., 1996; D'Orazio et al., 1997). Moreover, PEA3 and AP1 elements are also present in the promoters of the stromelysin and collagenase genes (Gutman and Wasylyk, 1990; Sirum-Conolly and Brinckerhoff, 1991) and these elements provide targets for transcriptional activation by specific transforming oncogenes (Wasylyk et al., 1989, 1993). In these contexts, the increased AP1 and PEA3 activity in E11-NMT cells versus E11 can result in elevated PEG-Prom activity and thereby increased PEG-3 protein which can directly contribute to cancer aggressiveness, resulting in enhanced tumor growth in vivo in nude mice, in the progressed tumor cells. The increased activity of AP1 and PEA3 in E11-NMT cells will also likely activate additional down-stream genes that can facilitate the cancer phenotype.

The mechanism by which PEG-3 facilitates expression of the transformed phenotype is not currently known. Forced expression of the rat PEG-3 gene in both rodent and human cancer cells results in an increase in anchorage independent growth and an augmentation in oncogenic potential (Su et al., 1997, 1999). One putative target for PEG-3 is the angiogenesis-inducing molecule, vascular endothelial growth factor (VEGF) (Su et al., 1999). Stable elevated expression of PEG-3 results in increased VEGF RNA transcription, steady-state mRNA and secreted protein in E11 cells. Moreover, a VEGF-luciferase reporter construct displays enhanced activity in cells expressing PEG-3. A functional role for PEG-3 in regulating VEGF expression is demonstrated further by inhibiting PEG-3 expression in E11-NMT cells using a stable antisense PEG-3 expression vector which results in a decrease in VEGF mRNA and secreted protein. The requirement for PEG-3 protein in inducing VEGF expression was demonstrated by simultaneous treatment of PEG-3 transfected cells with the protein synthesis inhibitor cycloheximide (Su et al., 1999). In this experiment, the transtected PEG-3 gene was expressed as PEG-3 mRNA, whereas VEGF mRNA was only present in cells not exposed to cycloheximide. Although it is not presently known if PEG-3 binds directly to the VEGF promoter or activation of VEGF transcription occurs by means of additional molecules, these studies suggest an association between PEG-3 expression, induction of angiogenesis and facilitation of expression of the cancer state.

Further studies are necessary to identify and characterize the repertoire of down-stream genes modulated as a consequence of PEG-3 expression and to determine their roles in facilitating cancer aggressiveness and angiogenesis. These investigations are important and offer potential for defining the genetic elements which are critical determinants of the cancer phenotype. With this information it will be possible to distinguish potential targets and define appropriate reagents, such as antisense or small molecule antagonists, for inhibiting or preventing cancer its development and progression.

Materials and Methods

Cell Cultures

E11 is a single cell clone of H5ts125-transformed Sprague-Dawley secondary RE cells (Fisher et al., 1978). E11-NMT is a subclone of E11 cells derived from a nude mouse tumor induced by the E11 cell line (Babiss et al., 1985). R12 is a Ha-ras oncogene transformed E11 clone (Duigou et al., 1989). F1 and F2 are suppressed somatic cell hybrids with a flat morphology that were formed between E11-NMT and CREF cells (Duigou et al., 1990). R1 and R2 are progressed somatic cell hybrids with a round morphology that were created by fusing E11-NMT and CREF cells (Duigou et al., 1990). CREF is a specific immortal non-transformed and non-tumorigenic clone of Fischer rat embryo fibroblast cells (Fisher et al., 1982). All cultures were grown in Dulbecco's modified Eagle's medium (DMEM) supplemented with 5% FBS (DMEM-5) at 37° C. in a humidified 5% $CO_2$ 95% air incubator.

Northern and Western Blotting Assays.

Total cellular RNA was isolated by the guanidinium/phenol extraction method and Northern blotting was performed as described (Su et al., 1994, 1997). Fifteen μg of RNA were denatured and electrophoresed in 1.2% agarose gels with 3% formaldehyde, transferred to nylon membranes and hybridized sequentially with $^{32}$P-labeled cDNA probes as described previously (Su et al., 1994, 1997). Following hybridization, the filters were washed and exposed for autoradiography. Western blotting analyses (Su et al., 1995) detected cJun (AP1), PEA3, PEG-3 and actin proteins. Five million cells were seeded into 100-mm plates and incubated for 24 h at 37° C. The medium (DMEM-5) was removed, the cells were washed 3× with cold PBS and then lysed in RIPC buffer (0.5 M NaCl, 0.5% NP40, 20 mM Tris-HCl, pH 8, 1 mM PMSF). The protein levels were determined using an ECL kit (Amersham) and the respective antibodies (Santa Cruz). Cell lysates were also analyzed using rabbit anti-PEC-3 polyclonal antibodies against C-terminal peptides.

Isolation and Analysis of the PEG-3 Promoter

Based on the 5' sequence of the PEG-3 cDNA, two nested primers with the sequences GATCTAGGGTGTTGT-GAGAGGATCGGAG (SEQ ID NO:2) and TCGGTTTGC-CAAAAGCGATCGTGGG (SEQ ID NO:3) were used with a Genome Walker Kit (Clontech) to obtain a genomic sequence containing the putative promoter of PEG-3. Three DNA fragments of 2.0-, 1.6- and 1.0-kb, respectively, with identical and overlapping nucleotide sequences were obtained using this approach. The 2.0-kb PEG-3 fragment (designated FL-PEG-Prom) was cloned into the pGL3-basic Vector (Promega) for promoter activity analysis. 5'-Deletion mutations in the FL-PEG-Prom were made with exonuclease III digestion using the Erase-A-Base System (Promega). 3'-Deletion mutations of the FL-PEG-Prom were made by digestion with BstEII/XhoI, SacII/XhoI and NdeI/XhoI, respectively. EstEII, SacII and NdeI are 20 single-cut restriction endonucleases recognizing DNA sequences in the FL-PEG-Prom, XhoI restriction site is located in the MCS of pGL3 vector near the 3' end of the FL-PEG-Prom. The internal deletions were performed by digesting the FL-PEG-Prom with NdeI/SacII, NdeI/BstEII, StuI/BstEII and BstXI, respectively. Mutations in the AP1-binding site, PEA3-binding site, and TATA box were made using a sitespecific mutagenesis method with the Altered Sites II In Vitro Mutagenesis System (Promega). The PEG-Prom deletion mutants were cloned into the pGL3-basic Luciferase Reporter Vector (Promega). To evaluate the activity of the various PEG-Prom-luciferase constructs, cells were seeded at 2×10⁵/35-mm tissue culture plate and ~24 h later transfected with 5 µg of the various PEG-Prom-luciferase constructs plus 1 µg of SV40-β-gal Vector (Promega) mixed with 10 µl of Lipofectamine Reagent (Gibco) in 200 µl of serum-free media. After 20 min at RT, 800 µl of serum-free media were added resulting in a final volume of 1 ml. The transfection mixture was removed after 14 hr and the cells were washed 3× with serum-free media and incubated at 37° C. for an additional 48 hr in complete growth media. Cells were harvested and lysed to make extracts (Gopalkrishnan et al., 1999) utilized in β-gal and Luciferase reporter assays. Luminometric determinations of Luciferase and Pgal activity was performed using commercial kits (Promega and Tropix, respectively). For Luciferase assays, 10 µl of cell lysate were mixed with 40 µl of Luciferase Assay substrate (Promega). For β-gal assays, 10 µl of the cell lysate were mixed with 100 µl of diluted Galecton-Plus with 150 µl of Accelerator (Tropix). Promoter analysis data were collected a minimum of three times using triplicate samples for each experimental point and the data was standardized with the l-gal data.

Primer Extension of E11 and E11-NMT mRNA

A primer with the sequence 5' GGCAAAGGGATGCG-GAGTCGCGCGGGTCTCGCATG 3' (SEQ ID NO:4) complementary to the 5' UTR sequence of the PEG-3 cDNA was annealed to 4 µg of PolyA⁺ RNAs from E11 or E11-NMT cells, which were used as template for primer extension with reverse transcriptase. In brief, 20 pmol of dephosphorylated oligo-DNA was end-labeled with $\gamma$-$^{32}$P ATP (Amersham) and T4 polynucleotide kinase. The labeled oligonucleotides (5×10⁵ cpm) were incubated with 4 µg of polyA+ RNA and the precipitate was resuspended in DEPC-treated H₂O. The reverse transcription reaction contained 200 u/µl of Superscript Reverse Transcriptase II (Gibco), 50 mM of Tris-HCl (pH 8.3), 40 mM KCl, 6 mM MgCl21 1 mM DTT, 1 mM dNTP, and 0.1 mg/ml BSA. The mixture was incubated at 42° C. for 1 hr followed by the addition of 1 ml of 0.5 M EDTA (pH 8) to stop the reaction. After DNase-free RNase treatment, the reaction mixture was loaded onto a 5% urea polyacrylamide sequencing gel in parallel with a DNA sequencing reaction using the same primer and template.

Electrophoretic Mobility Shift Assays (EMSA)

Nuclear extracts were prepared from 2 to 5×10⁸ cells as described by Dignam et al. (1983). The sequence of probes were as follows: wild-type AP1, 5' CGCAGAT TGACTCAGTTCGC3' (SEQ ID NO:5)/3" GCGTCTA ACTGAGTCAAGCG 5' (SEQ ID NO:6); mutant AP1, 5' CGCAGATAAACTACGTTCGC 3' (SEQ ID NO:7)/3' GCGTCTATTTGATGCAAGCG 5' (SEQ ID NO:8); wild-type PEA3, 5' GTGTTGTTTTCCTCTCTCCA 3' (SEQ ID NO:9)/3' CACAACAAAAGGAGAGAGGT 5' (SEQ ID NO:10); and mutant PEA3', 5' GTGTTGT TCCCATCTCTCCA 3' (SEQ ID NO:11)/3' CACAACA AGGGTAGAGAGGT 5' (SEQ ID NO:12). The double-stranded oligonucleotides were labeled with $^{32}$P-ATP (Amersham) arid T4 polynucleotide kinase. The labeled probes were then incubated with nuclear extract at RT for 30 min. The reaction mixture consisted of $^{32}$P-labeled deoxy-nucleotides (>5000 cpm), 2 µg of poly(dl-dc) and 10 µg of nuclear protein extract with 10 mM HEPES (pH 7.5), 50 mM KCl, 5 mM MgCl2, 0.5 mM EDTA, 1 mM DTT and 12.5% glycerol. After incubation for 30 min at RT, the reaction mixtures were electrophoresed on a 5% polyacrylamide gel with 0.5×TBE (160V for 3 h). The gel was dried and autoradiographed. Nuclear extracts were also incubated with a 10- or 100-fold molar excess of cold competitor oligonucleotide or cJun (AP1), PEA3 or actin antibody (1 or 5µ together with the $^{32}$P-labeled probe.

References

1. Angel, P. & Karin, M. (1991). *Biochim. Biophys. Acta*, 1072, 129–157.
2. Babiss, L. E., Zimmer, S.G. & Fisher, P. B. (1985). *Science*, 228, 1099–1101.
3. Bishop, J. M. (1991). *Cell*, 64, 235–248.
4. Brown, T. A. & McKnight, S. L. (1992). *Genes & Develop.*, 6, 2502–2512.
5. De Cesare, D., Palazzolo, M. & Blasi F. (1996). *Oncogene*, 13, 2551–2562.
6. Dignam, J. M., Lebovitz, R. M. & Roeder, R. G. (1983). *Nucl. Acids Res.*, 11, 1475–1489.
7. D'Orazio D., Besser, D., Marksitzer, R., Kunz, C., Hume, D. A., Kiefer, B. & Nagamine, Y. (1997). Gene, 201, 179–187.
8. Duigou, G. J., Babiss, L. E. & Fisher, P. B. (1989). *NY Acad. Sci.*, 567, 302–306.
9. Duigou, G. J., Babiss, L. E., Iman, D. S., Shay, J. W. & Fisher, P. B. (1990). *Mol. Cell. Biol.*, 10, 2027–2034.
10. Duigou, G. J., Su, Z.-z., Babiss, L. E., Driscoll, B., Fung, Y.-K. T. & Fisher, P. B. (1991). *Oncogene*, 6, 1813–1824.
11. Edwards, D. R., Rocheleau, H., Sharma, R. S., Wils, A. J., Cowie, A., Hassell, J. A. & Heath, J. K. (1992). *Biochem. Biophys. Acta*, 1171, 41–55.
12. Fisher, P. B. (1984). *In: Tumor Promotion and Cocarcinogenesis In Vitro, Mechanisms of Tumor Promotion*. Slaga T. J. (ed). CRC Press, Inc., Boca Raton, Fla., pp. 57–123.

13. Fisher, P. B., Weinstein, I. B., Eisenberg, D. & Ginsberg, H. S. (1978). *Proc. Natl. Acad. Sci. USA*, 75, 2311–2314.
14. Fisher, P. B., Goldstein, N. I. & Weinstein, I. B. (1979a). *Cancer Res.*, 39, 3051–3057.
15. Fisher, P. B., Dorsch-Hasler, K., Weinstein, I. B. & Ginsberg, H. S. (1979b). *Nature*, 281, 591–594.
16. Fisher, P. B., Bozzone, J. H. & Weinstein, I. B. (1979c). *Cell*, 18, 695–705.
17. Fisher, P. B., Babiss, L. E., Weinstein, I. B. & Ginsburg, H. S. (1982). *Proc. Natl. Acad. Sci. USA*, 79, 3527–3531.
18. Gopalkrishnan, R. V., Christiansen, K., Goldstein, N. I., DePinho, R. A. & Fisher, P. B. (1999). *Nucl. Acids Res.*, in press.
19. Gutman, A. & Wasylyk, B. (1990). *EMBO J.*, 9, 2241–2246.
20. Hartwell, L. H. & Kastan, M. B. (1994). *Science*, 266, 1821–1828.
21. Higashino, F., Yoshida, K., Noumi, T., Seiki, M. & Fujinaga, K. (1995). *Oncogene*, 10, 1461–1463.
22. Jiang, H. & Fisher, P. B. (1993). *MoL Cell. Different*, 1, 285–299.
23. Kang, D.-c., LaFrance, R., Su, Z.-z. & Fisher, P. B. (1998a). *Proc. Natl. Acad. Sci. USA*, 95, 13788–13793.
24. Kang, D.-c., Motwani, M. & Fisher, P. B. (1998b). *Intl. J. Oncology*, 13, 1117–1126.
25. Karin, M., Liu, Z. & Zandi, E. (1997). *Curr. Opin. Cell Biol.*, 9, 240–246.
26. Kohn, E. C. & Liotta, L. A. (1995). *Cancer Res.*, 55, 1856–1862.
27. Knudson, A. G. (1993). *Proc. Natl. Acad. Sci. USA*, 90, 10914–10921.
28. Levine. A. J. (1993). *Annu. Rev. Biochem.*, 62, 623–651.
29. Liofta, L. A., Steeg, P. G. & Stetier-Stevenson, W. G. (1991). *Cell*, 64, 327–336.
30. Matrisian, L. M. & Bowden, G. T. (1990). *Sem. Cancer Biol.*, 1, 107–115.
31. Matrisian, L. M. (1994). *Ann. NY Acad. Sci.*, 91, 10129–10133.
32. Macleod, K., Leprince, D. & Stehelin, D. (1992). *Trends Biochem. Sci.*, 17, 251 256.
33. Nerlov, C., De Cesare, D., Pergola, F., Caracciolo, A., Blasi, F., Johnsen, M. & Verde, P. (1992). *EMBO J.*, 11, 4573–4582.
34. Olive, M., Krylov, D., Echlin, D. R., Gardner, K., Taparowsky, E. & Vinson, C.(1997). *J. BioL Chem.*, 272, 18586–18594
35. Reddy, P. G., Su, Z.-z. & Fisher, P. B. (1993). In: *Chromosome and Genetic Analysis, Methods in Molecular Genetics*. Adolph K. W. (ed). Vol 1. Academic Press, Inc., Orlando, Fla., pp. 68–102.
36. Seth, A., Ascione, R., Fisher, R. J., Mavrothalassitis, G. J., Bhat, N. K. & Papas, T. S. (1992). *Cell Growth & Different.*, 3, 327–334.
37. Sirum-Conolly, K. & Brinckerhoff, C. E. (1991). *Nucl. Acids Res.*, 19, 335–341.
38. Stacey, K. J., Fowles, L. F., Colman, M. S., Ostrowski, M. C. & Hume, S. A. (1995). *Mol. Cell. BioL*, 15, 3430–3441.
39. Su, Z.-z., Shen, R., O'Brian, C. A. & Fisher, P. B. (1994). *Oncogene*, 9, 1123–1132.
40. Su, Z.-z., Yemul, S., Estabrook, A., Zimmer, S. G., Friedman, R. M. & Fisher, P. B. (1995). *Intl. J. Oncology*, 7, 1279–1284.
41. Su, Z.-z., Shi, Y. & Fisher, P. B. (1997). *Proc. Natl. Acad. Sci. USA*, 94, 9125–9130.
42. Su, Z.-z., Goldstein, N. I., Jiang, H., Wang, M.-N., Duigou,
43. G. J., Young, C. S. H. & Fisher, P. B. (1999). *Proc. Natl. Acad. Sci. USA*, 96, 15115–15120.
44. Vogelstein, B. & Kinzier, K. W. (1993). *Trends Genet.*, 9, 138–141.
45. Wasylyk, C., Flores, P., Gutman, A. & Wasylyk, B. (i 989). *EMBO J.*, 8, 3371 3378.
46. Wasylyk, B., Hahn, S. L. & Giovane, A. (1993). *Eur. J. Biochem.*, 211, 7–18.

What is claimed is:

1. An isolated nucleic acid comprising a PEG-3 promoter comprising:
   (i) a PEA3 protein binding sequence consisting of the nucleotide sequence beginning with the thymidine (T) at position 1672 and ending with the thymidine (T) at position 1677 of SEQ ID NO:1,
   (ii) a TATA sequence consisting of the nucleotide sequence beginning with the thymidine (T) at position 1748 and ending with the adenosine (A) at position 1753 of SEQ ID NO:1, and
   (iii) an AP1 protein binding sequence consisting of the nucleotide sequence beginning with the thymidine (T) at position 1781 and endina with the adenosine (A) at position 1787 of SEQ ID NO:1.

2. The isolated nucleic acid of claim 1, wherein the entire length of the PEG-3 promoter is at least about 99% identical to the sequence of nucleotides 1507 to 1970 of SEQ ID NO:1.

3. An isolated nucleic acid comprising a PEG-3 promoter comprising:
   (i) a PEA3 protein binding sequence consisting of the nucleotide sequence beginning with the thymidine (T) at position 1672 and ending with the thymidine (T) at position 1677 of SEQ ID NO:1,
   (ii) a TATA sequence consisting of the nuclectide sequence beginning with the thymidine (T) at position 1748 and ending with the adenosine (A) at position 1753 of SEQ ID NO:1, and
   (iii) an AP1 protein binding sequence consisting of the nucleotide sequence beginning with the thymidine (T) at position 1781 and ending with the adenosine (A) at position 1787 of SEQ ID NO:1,
   wherein said PEG-3 promoter is at least about 464 nucleotides long and has PEG-3 promoter activity.

4. An isolated nucleic acid comprising a PEG-3 promoter comprising the nucleotide sequence beginning with the guanosine (G) at position 1507 and ending with the cytosine (C) at position 1970 of SEQ ID NO:1.

5. The nucleic acid of claim 4, wherein the nucleic acid is operably linked to a gene of interest.

6. The nucleic acid of claim 5, wherein the gene of interest is a reporter gene.

7. The nucleic acid of claim 6, wherein the reporter gene encodes beta-galactosidase, luciferase, chloramphenicol transferase or alkaline phosphatase.

8. The nucleic acid of claim 5, wherein the gene of interest is a tumor suppressor gene, a gene whose expression causes apoptosis of a cell, or a cytotoxic gene.

9. A vector comprising the nucleic acid of any one of claims 4 and 5 to 8.

10. A host cell comprising the vector of claim 9.

11. The host cell of claim 10, wherein the host cell is a tumor cell.

12. The host cell of claim 11, wherein the tumor cell is a melanoma cell, a neuroblastoma cell, a cervical cancer cell, a breast cancer cell, a lung cancer cell, a prostate cancer cell, a colon cancer cell or a glioblastoma multiforme cell.

* * * * *

UNITED STATES PATENT AND TRADEMARK OFFICE
CERTIFICATE OF CORRECTION

PATENT NO. : 6,737,523 B1  
APPLICATION NO. : 09/621781  
DATED : May 18, 2004  
INVENTOR(S) : Fisher et al.

Page 1 of 1

It is certified that error appears in the above-identified patent and that said Letters Patent is hereby corrected as shown below:

Title Page; item (63); and col. 1, line 9;  
Please make the following correction in the Related U.S. Application Data Section:

Replace "6,472,320" with --6,472,520--

Signed and Sealed this

Fifteenth Day of April, 2008

JON W. DUDAS  
*Director of the United States Patent and Trademark Office*